United States Patent
Warren et al.

(10) Patent No.: US 8,080,416 B2
(45) Date of Patent: **\*Dec. 20, 2011**

(54) METHOD FOR DETERMINING THE IMMUNOGENICITY OF AN ANTIGEN

(75) Inventors: William L. Warren, Orlando, FL (US); Donald Drake, III, Orlando, FL (US); Janice Moser, Orlando, FL (US); Inderpal Singh, Orlando, FL (US); Haifeng Song, Oviedo, FL (US); Eric Mishkin, Winter Springs, FL (US)

(73) Assignee: Sanofi Pasteur Vaxdesign Corp., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/707,522

(22) Filed: Feb. 17, 2010

(65) Prior Publication Data

US 2010/0166763 A1   Jul. 1, 2010

Related U.S. Application Data

(60) Division of application No. 11/594,172, filed on Nov. 8, 2006, now Pat. No. 7,785,806, which is a continuation-in-part of application No. 11/453,046, filed on Jun. 15, 2006, which is a continuation-in-part of application No. 11/116,234, filed on Apr. 28, 2005, now Pat. No. 7,855,074.

(60) Provisional application No. 60/565,846, filed on Apr. 28, 2004, provisional application No. 60/643,175, filed on Jan. 13, 2005.

(51) Int. Cl.
   *C12N 5/00* (2006.01)
   *C12N 5/08* (2006.01)

(52) U.S. Cl. ............... 435/347; 435/372.2; 435/372.3; 435/372

(58) Field of Classification Search ............. None
   See application file for complete search history.

(56) References Cited

U.S. PATENT DOCUMENTS

| | | | |
|---|---|---|---|
| 5,008,116 A | 4/1991 | Cahn | |
| 5,160,490 A | 11/1992 | Naughton et al. | |
| 5,354,686 A | 10/1994 | Haberman | |
| 5,562,910 A | 10/1996 | Daynes et al. | |
| 5,725,856 A | 3/1998 | Hudziak et al. | |
| 5,739,001 A | 4/1998 | Brown et al. | |
| 5,750,329 A | 5/1998 | Quinn et al. | |
| 6,177,282 B1 | 1/2001 | McIntyre | |
| 6,274,378 B1 | 8/2001 | Steinman et al. | |
| 6,479,064 B1 | 11/2002 | Atala | |
| 6,541,225 B1 * | 4/2003 | Li | 435/69.6 |
| 6,835,550 B1 | 12/2004 | Estell et al. | |
| 7,709,257 B2 * | 5/2010 | Tew et al. | 435/373 |
| 2002/0155108 A1 | 10/2002 | Barbera-Guillem et al. | |
| 2003/0109042 A1 | 6/2003 | Wu et al. | |
| 2003/0147923 A1 | 8/2003 | Klaviniskis | |
| 2003/0199006 A1 | 10/2003 | Britz et al. | |
| 2003/0207287 A1 | 11/2003 | Short | |
| 2004/0009943 A1 | 1/2004 | Semple et al. | |
| 2004/0109876 A1 | 6/2004 | Yamamoto et al. | |
| 2004/0234510 A1 | 11/2004 | Mochitate | |
| 2005/0191743 A1 | 9/2005 | Wu et al. | |
| 2005/0229264 A1 | 10/2005 | Chang et al. | |
| 2005/0282148 A1 | 12/2005 | Warren et al. | |
| 2006/0078540 A1 | 4/2006 | Warren et al. | |
| 2006/0105454 A1 | 5/2006 | Son et al. | 435/325 |
| 2006/0270029 A1 | 11/2006 | Warren et al. | |
| 2006/0275270 A1 | 12/2006 | Warren et al. | |
| 2007/0015136 A1 | 1/2007 | Sanchez-Schmitz et al. | |
| 2007/0141552 A1 | 6/2007 | Warren et al. | |
| 2007/0154956 A1 | 7/2007 | Warren et al. | |
| 2007/0178076 A1 | 8/2007 | Drake et al. | |
| 2007/0218054 A1 | 9/2007 | Sukumar et al. | |
| 2008/0008653 A1 | 1/2008 | Tew et al. | |
| 2009/0011455 A1 | 1/2009 | Warren et al. | |
| 2009/0104221 A1 | 4/2009 | El Shikh et al. | |
| 2009/0117581 A1 | 5/2009 | Warren et al. | |

FOREIGN PATENT DOCUMENTS

| | | |
|---|---|---|
| EP | 0358506 | 9/1989 |
| EP | 1013668 A1 | 6/2000 |
| EP | 1437147 | 9/2002 |
| EP | 1970444 | 12/2006 |
| WO | 99/12972 | 3/1999 |
| WO | WO 99/15629 | 4/1999 |
| WO | WO 99/43788 | 9/1999 |
| WO | WO 99/49319 | 9/1999 |
| WO | WO 03/041568 | 5/2003 |
| WO | WO 03/050271 | 6/2003 |
| WO | WO 2004/031361 | 4/2004 |
| WO | WO 2004/101773 | 11/2004 |
| WO | 2005/013896 | 2/2005 |
| WO | 2005/072088 | 8/2005 |
| WO | WO 2005/104755 | 11/2005 |
| WO | WO 2007/075979 | 7/2007 |
| WO | 2007/108835 | 9/2007 |
| WO | WO 2007/106559 | 9/2007 |
| WO | WO 2007/146267 | 12/2007 |

OTHER PUBLICATIONS

Buchler et al., Vaccine, 2003, v.21, pp. 877-882).*
Ansel, et al., "A Chemokine-Driven Positive Feedback Loop Organizes Lymphoid Follicles", Nature, vol. 406, pp. 309-314 (2000).
Aydar et al. (2005) *J. Immunol.* 174, 5358-5366.
Badylak, S.F. et al., "Small Intestinal Submucosa: A Substrate for in vitro Cell Growth," J. Biomater. Sci. Polymer Edn. (1998), vol. 9, No. 8, pp. 863-878.

(Continued)

*Primary Examiner* — Michail Belyavskyi
(74) *Attorney, Agent, or Firm* — Roylance, Abrams, Berdo & Goodman, L.L.P.

(57) ABSTRACT

The present invention relates to methods for preparing an artificial immune system. The artificial immune system comprises a cell culture comprising T cells, B cells and antigen-primed dendritic cells. The artificial immune system of the present invention can be used for in vitro testing of vaccines, adjuvants, immunotherapy candidates, cosmetics, drugs, biologics and other chemicals.

14 Claims, 16 Drawing Sheets

OTHER PUBLICATIONS

Bai et al., "*Generation of Dendritic Cells From Human Bone Marrow Mononuclear Cells: Advantages From Clinical Applications in Comparison to Peripheral Blood Monocyte Derived Cells*," International Journal of Oncology, (2002), 20(2), pp. 247-253.

Banchereau, et al., "Dendritic Cells and the Control of Immunity", Nature, vol. 392, pp. 245-252 (1998).

Banchereau, et al., "Immunobiology of Dendritic Cells", Annu. Rev. Immunol., vol. 18, pp. 767-811 (2000).

Baumgarth, "A Two-Phase Model of B-Cell Activation", Immunological Review, vol. 176, pp. 171-180 (2000).

Benbrook et al., "Organotypic cultures represent tumor microenvironment for drug testing," Drug Discovery Today: Disease Models, 3(2), pp. 143-148 (2005).

Berman, et al., "Roles of Platelet/Endothelial Cell Adhesion Molecule-1 (PECAM-1, CD31) in Natural Killer Cell Transendothelial Migration and Beta 2 Integrin Activation", The Journal of Immunology, vol. 156, pp. 1515-1524 (1996).

Birkness et al., A Tissue Culture Bilayer Model to Study the Passage of *Neisseria meningitidis, Infection and Immunity*, Feb. 1995, p. 402-409, vol. 63, No. 2.

Birkness et al., An In Vitro Tissue Culture Bilayer Model to Examine Early Events in *Mycobacterium tuberculosis* Infection, *Infection and Immunity*, Feb. 1999, p. 653-658, vol. 67, No. 2.

Bogdan, et al., "Fibroblasts as Host Cells in Latent Leishmaniosis", *J. Exp. Med.*, vol. 191, pp. 2121-2129 (2000).

Boni et al. (2006) *Eur. J. Immunol.* 36, 3157-3166.

Brandtzaeg, P. et al., "*Mucosal B Cells: Phenotypic Characteristics, Transcriptional, Regulation, and Homing Properties*," Immunological Reviews (2005), vol. 206, pp. 32-63.

Bromelow, K. V. et al., "*Whole Blood Assay for Assessment of the Mixed Lymphocyte Reaction*," Journal of Immunological Methods, (2001), 247(1-2), pp. 1-8.

Büchele, S. et al., "*Presentation of Tetanus Toxoid to Autologous T Cells by Dendritic Cells Generated From Human Blood. Improved Specificity With Dendritic Cells Generated Without Fetal Calf Serum*," Advances in Experimental Medicine and Biology, (1997), vol. 417, pp. 233-237.

Buchler et al. (2003) *Vaccine*, 21, 877-882.

Butcher, et al., "Lymphocyte Trafficking and Regional Immunity", Advances in Immunology, vol. 72, pp. 209-253 (1999).

Castro, et al., "Spleen-Derived Stromal Cells. Adhesion Molecules Expression and Lymphocyte Adhesion to Reticular Cells", Eur. J. Cell. Biol., vol. 74, 321-328 (1997).

Caux et al. (1995) *J. Immunol.* 155, 5427-5435.

Cayeux et al. (1999) *Eur. J. Immunol.* 29, 225-234.

Chen, et al., "A Film Tension Theory of Phagocytosis", Journal of Colloid and Interface Science, vol. 190, pp. 118-133 (1997).

Chou, et al., "The Detection of the HLA-B27 Antigen by Immunomagnetic Separation and Enzyme-Linked Immunosorbent Assay-Comparison with a Flow Cytometric Procedure", Journal of Immunological Methods, vol. 255, pp. 15-22 (2001).

Clayton et al., Clin. Exp. Immunol., 2003, v.132, p. 174-179.

Crivellato, et al., "Stromal Cell Organisation in the Mouse Lymph Node. A Light and Electron Microscopic Investigation Using the Zinc Iodide-Osmium Technique", J. Anat., vol. 190, pp. 85-92 (1997).

Cyster, "Chemokines and the Homing of Dendritic Cells to the T Cell Areas of Lymphoid Organs", J. Exp. Med. vol. 189, No. 3, pp. 447-450 (1999).

Cyster, et al., "Follicular Stromal Cells and Lymphocyte Homing to Follicles", Immunological Reviews, vol. 176, pp. 181-193 (2000).

D'Amico et al., Blood 92:207-214 (1998).

Danke, et al., "HLA Class II-Restricted CD4+ T Cell Responses Directed Against Influenza Viral Antigens Postinfluenza Vaccination", The Journal of Immunology, vol. 171, pp. 3163-3169 (2003).

Denkbas, et al., "Magnetic Chotosan Microspheres: Preparation and Characterization", Reactive & Functional Polymers, vol. 50, pp. 225-232 (2002).

Dubey et al. (2005) *J. Clin. Endocrin & Met.*, 90, 247-255.

Dubois, et al., "Dendritic Cells Enhance Growth and Differentiation of CD40-Activated B Lymphocytes", J. Exp. Med., vol. 185, pp. 941-951 (1997).

Dubois et al., J. Leukocyte Biology, 1999, v.66, p. 224-230.

Edelman et al, A Cultureal Renaissance: In Vitro Cell Biology Embraces Three-Dimensional Context. Exp Neurol. 2005, vol. 192, pp. 1-6.

El Shikh, M. et al., "*Follicular Dendritic Cells Stimulated by Collagen Type I Develop Dendrites and Networks In Vitro*," Cell and Tissue Research, (2007), 329(1), pp. 81-89.

Forster, et al., "CCR7 Coordinates the Primary Immune Response by Establishing Functional Microenvironments in Secondary Lymphoid Organs", Cell., vol. 99, pp. 23-33 (1999).

Fransson, et al., "Culture of Human Epidermal Langerhans Cells in a Skin Equivalent", British Journal of Dermatology, vol. 139, pp. 598-604 (1998).

Friedl, et al., "CD4+ T Lymphocytes Migrating in Three-Dimensional Collagen Lattices Lack Focal Adhesions and Utilize Beta 1 Integrin-Independent Strategies for Polarization, Interaction with Collagen Fibers and Locomotion", Eur. J. Immunol., vol. 28, pp. 2331-2343 (1998).

Fulcher, et al., "B-Cell Activation Versus Tolerance—The Central Role of Immunoglobulin Receptor Engagement and T-Cell Help", Int. Rev. Immunol., vol. 15, pp. 33-52 (1997).

Furie, et al., "Migration of Neutrophils Across Endothelial Monolayers is Stimulated by Treatment of the Monolayers with Interleukin-1 or Tumor Necrosis Factor-Alpha", The Journal of Immunology, vol. 143, pp. 3309-3317 (1989).

Furuyama, A. et al., "*Assembly of Basement Membrane in vitro by Cooperation Between Alveolar Epithelial Cells and Pulmonary Fibroblasts*," Cell Structure and Function (1997), vol. 22, pp. 603-614.

Galibert, et al., "CD40 and B Cell Antigen Receptor Dual Triggering of Resting B Lymphocytes Turns on a Partial Germinal Center Phenotype", J. Exp. Med., vol. 183, pp. 77-85 (1996).

Gansuvd et al., Human Immunol., 2003, v.64, p. 427-439.

Garside, et al., "Visualization of Specific B and T Lumphocyte Interactions in the Lymph Node", Science, vol. 281, pp. 96-99 (1998).

Gergel, et al., "Activation of Endothelium by *Borrelia burgdorferi* In Vitro Enhances Transmigration of Specific Subsets of T Lymphocytes", Infection and Immunity, vol. 69, pp. 2190-2197 (2001).

Gretz, et al., "Cords, Channels, Corridors and Conduits: Critical Architectural Elements Facilitating Cell Interactions in the Lymph Node Cortex", Immunological Reviews, vol. 156, pp. 11-24 (1997).

Gretz, et al., "Lymph-borne Chemokines and Other Low Molecular Weight Molecules Reach High Endothelial Venules Via Specialized Conduits While a Functional Barrier Limits Access to the Lymphocyte Microenvironments in Lymph Node Cortex", The Journal of Experimental Medicine, vol. 192, pp. 1425-1439 (2000).

Gretz, et al., "Sophisticated Strategies for Information Encounter in the Lymph Node: The Reticular Network as a Conduit of Soluble Information and a Highway for Cell Traffic", The Journal of Immunology, vol. 157, pp. 495-499 (1996).

Gundersen, et al., "Magnetic Bead Antigen Capture Enzyme-Linked Immunoassay in Microtitre Trays for Rapid Detection of Schistosomal Circulating Anodic Antigen", Journal of Immunological Methods, vol. 148, pp. 1-8 (1992).

Gunn, et al., "Mice Lacking Expression of Secondary Lymphoid Organ Chemokine Have Defects in Lymphocyte Homing and Dentritic Cell Localization", J. Exp. Med., vol. 189, pp. 451-460 (1999).

Gunzer, et al., "Antigen Presentation in Extracellular Matrix: Interactions of T Cells with Dendritic Cells are Dynamic, Short Lived, and Sequential", Immunity, vol. 13, pp. 323-332 (2000).

Hasbold, et al., "Quantitative Analysis of Lymphocyte Differentiation and Proliferation in Vitro Using CarboxyFluorescein Diacetate Succinimidyl Ester", Immunology and Cell Biology, vol. 77, pp. 516-522 (1999).

Irvine, et al., "Nanoscale Clustering of RGD Peptides at Surfaces Using Comb Polymers. 1. Synthesis and Characterization of Comb Thin Films", Biomacromolecules, vol. 2, pp. 85-94 (2001).

Jenkins, et al., "In Vivo Activation of Antigen-Specific CD4 T Cells", Annu. Rev. Immunol., vol. 19, pp. 23-45 (2001).

Ansel, et al., "A Chemokine-Driven Positive Feedback Loop Organizes Lymphoid Follicles", Nature, vol. 406, pp. 309-314 (2000).
Aydar et al. (2005) *J. Immunol.* 174, 5358-5366.
Badylak, S.F. et al., "*Small Intestinal Submucosa: A Substrate for in vitro Cell Growth*," J. Biomater. Sci. Polymer Edn. (1998), vol. 9, No. 8, pp. 863-878. Junt, et al., "Antiviral Immune Responses in the Absence of Organized Lymphoid T Cell Zones in *plt/plt* Mice", The Journal of Immunology, vol. 168, pp. 6032-6040 (2002).
Kabashima, et al., "Prostaglandin $E_2$-EP4 Signaling Initiates Skin Immune Responses by Promoting Migration and Maturation of Langerhans Cells", Nature Medicine, vol. 9, pp. 744-749 (2003).
Kadowaki, et al., "Subsets of Human Dendritic Cell Precursors Express Different Toll-Like Receptors and Respond to Different Microbial Antigens", J. Exp. Med. vol. 194, No. 6, pp. 863-869 (2001).
Kaldjian, et al., "Spatial and Molecular Organization of Lymph Node T Cell Cortex: A Labyrinthine Cavity Bounded by an Epithelium-Like Monolayer of Fibroblastic Reticular Cells Anchored to Basement Membrane-like Extracellular Matrix", International Immunology, vol. 13, pp. 1243-1253 (2001).
Khademhosseini et al., "Microscale Technologies for Tissue Engineering and Biology," Proc. Natl. Acad. Sci. USA, vol. 103, pp. 2480-2487 (2006).
Kim et al., "*Three-Dimensional Tissue Culture Models in Cancer Biology*," Seminars in Cancer Biology, (2005), 15(5), pp. 365-377.
Kim, H.-J. et al, Establishment of Early Lymphoid Organ Infrastructure in Transplanted Tumors Mediated by Local Production of Lymphotoxin α and in Combined Absence of Functional B and T Cells. In J. of Immunology, vol. 172:4037-4047 (2004).
Kosco, M. H. et al., "*Folicular Dendritic Cell-Dependent B-Cell Proliferation and In Vitro Germinal Center*," Lymphatic Tissues In Vivo Immune Responses, (1991), pp. 687-690.
Kosco, M. H. et al., "*Follicular Dendritic Cell-Dependent Adhesion and Proliferation of B Cells In Vitro*," Journal of Immunology, (1992), 148(8), pp. 2331-2339.
Kosco, M. H. et al., "*Follicular Dendritic Cells and Germinal Center Formation In-Vitro*," Accessory Cells in HIV and Other Retroviral Infections: Morphological and Functional Aspects; Workshop on Morphological and Functional Aspects of Accessory Cells in retroviral Infections, Hamberg, Germany, 23-24, p. 44-49 (1991).
Kosco-Vilbois, "Are Follicular Dendritic Cells Really Good for Nothing", Nature Reviews Immunology, vol. 3, pp. 764-769 (2003).
Kourilov, et al., "Magnetic-Bead Enzyme-Linked Immunosorbent Assay Verifies Adsorption of Ligand and Epitope Accessibility", Analytical Biochemistry, vol. 311, pp. 166-170 (2002).
Larsson, et al., "Requirement of Mature Dendritic Cells for Efficient Activation of Influenza A-Specific Memory CD8+ T Cells", The Journal of Immunology, vol. 165, pp. 1182-1190 (2000).
LeBedis, et al., "Peripheral Lymph Node Stromal Cells Can Promote Growth and Tumorigenicity of Breast Carcinoma Cells Through the Release of IGF-I and EGF", Int. J. Cancer, vol. 100, pp. 2-8 (2002).
Levenberg, S. et al., "*Advances in Tissue Engineering*," Current Topics in Developmental Biology, (2004), vol. 61, pp. 113-134.
Luk, et al., "Rapid and Sensitive Detection of *Salmonella* (O:6,7) by Immunomagnetic Monoclonal Antibody-Based Assays", Journal of Immunological Methods, vol. 137, pp. 1-8 (1991).
Lukas, et al., "Human Cutaneous Dendritic Cells Migrate Through Dermal Lymphatic Vessels in a Skin Organ Culture Model", The Journal of Investigative Dermatology, vol. 106, pp. 1293-1299 (1996).
Manna, P. et al., "Differentiation and Functional Maturation of Human CD14<+> Adherent Peripheral Blood Monocytes by Xenogeneic Endothelial Cells: Up-Regulation of Costimulation Cytokine Generation, and Toll-Like Receptors," Transplantation, (2002), 74(2), pp. 243-252.
Matsumoto, et al., "Affinity Maturation Without Germinal Centres in Lymphotoxin-α-Deficient Mice", Nature, vol. 382, pp. 462-466 (1996).
Mebius, "Organogenesis of Lymphoid Tissues", Nat. Rev. Immunol, vol. 3, pp. 292-303 (2003).
Mellman, et al., "Dendritic Cells: Specialized and Regulated Antigen Processing Machines", Cell, vol. 106, pp. 255-258 (2001).

Miller, et al., "Two-Photon Imaging of Lymphocyte Motility and Antigen Response in Intact Lymph Node", Science, vol. 296, pp. 1869-1873 (2002).
Mori, et al., "Mice Lacking Expression of the Chemokines CCL21-ser and CCL19 (plt Mice) Demonstrate Delayed but Enhanced T Cell Immune Responses", J. Exp. Med., vol. 193, No. 2, pp. 207-217 (2001).
Moser et al. (2000) *Nature Immunol.* 1, 199-205.
Nakamura, M. et al., "*Expression of Leptin in Two-layered Culture of Gastric Mucous Cells and Fibroblasts: Effect of Helicobacter pylori Attachment*," Aliment Pharmacol Ther. (2004), vol. 20, suppl. 1, pp. 125-130.
Nakatsu, M. N. et al., "*Angiogenic Sprouting and Capillary Lumen Formation Modeled by Human Umbilical Vein Endothelial Cells (HUVEC) in Fibrin Gels: The Role of Fibroblasts and Angiopoietin-1*," Microvascular Research (2003), vol. 66, pp. 102-112.
Neves, A. R. et al., "*Dendritic Cells Derived From Metastatic Cancer Vaccinated With Allogeneic Dendritic Cell-Autologous Tumor Cell Hybrids Express More CD86 and Induce Higher Levels of Interferon-Gamma in Mixed Lymphocyte Reactions*," Cancer Immunology and Immunotherapy, (2005), 54(1), pp. 61-66.
Oehler et al. (2000) *Ann. Hematol.*, 79, 355-362.
Okamoto et al, Artificial Lymph Nodes Induce Potent Secondary Immune Response in Naïve and Immunodeficient Mice. J. Clin. Invest. Apr. 2007, vol. 117, No. 4, pp. 997-1007.
Parker, "T Cell-Dependent B Cell Activation", Annu. Rev. Immunol., vol. 11, pp. 331-360 (1993).
Pasparakis, et al., "Immune and Inflammatory Responses in TNFα Deficient Mice: A Critical Requirement for TNFα in the Formation of Primary B Cell Follicles, Follicular Dendritic Cell Networks and Germinal Centers, and in the Maturation of the Humoral Immune Response", J. Exp. Med., vol. 184, pp. 1397-1411 (1996).
Phillips, et al., "Activation of Pertussis Toxin-Sensitive CXCL12 (SDF-1) Receptors Mediates Transendothelial Migration of T Lymphocytes Across Lymph Node High Endothelial Cells", Eur. J. Immunol., vol. 32, pp. 837-847 (2002).
Podgrabinska, et al., "Molecular Characterization of Lymphatic Endothelial Cells", Proc. Natl. Acad. Sci. U.S.A., vol. 99, No. 25, pp. 16069-16074 (2002).
Portner, R et al, Chapter 2: An Overview on Bioreactor Design, Prototyping, and Process Control for Reproducible Three-Dimensional Tissue Culture. In Drug Testing In Vitro: Breakthrough Cell Cultur Technology. Eds. U. Marx and V. Sandig 2006: Wiley-VCH, pp. 65-69.
Poznansky, et al., "Efficient Generation of Human T Cells From a Tissue-Engineered Thymic Organoid", Nature Biotechnology, vol. 18, pp. 729-734 (2000).
Qu, et al., "Autocrine Type I IFN and Contact with Endothelium Promote the Presentation of Influenza A Virus by Monocyte-Derived APC", The Journal of Immunology, vol. 170, pp. 1010-1018 (2003).
Randolph, et al., "A Physiologic Function for p-Glycoprotein (MDR-1) During the Migration of Dendritic Cells from Skin Via Afferent Lymphatic Vessels", Proc. Natl. Acad. Sci., vol. 95, pp. 6924-2929 (1998).
Randolph, et al., "A Soluble Gradient of Endogenous Monocyte Chemoattractant Protein-1 Promotes the Transendothelial Migration of Monocytes In Vitro", The Journal of Immunology, vol. 155, pp. 3610-3618 (1995).
Randolph, et al., "Differentiation of Monocytes into Dendritic Cells in a Model of Transendothelial Trafficking", Science, vol. 282, pp. 480-483 (1998).
Randolph, et al., "Mononuclear Phagocytes Egress from an In Vitro Model of the Vascular Wall by Migrating Across Endothelium in the Basal to Apical Direction: Role of Intercellular Adhesion Molecule 1 and the CD11/CD18 Integrins", J. Exp. Med., vol. 183, pp. 451-462 (1996).
Randolph, et al., "Role of Tissue Factor in Adhesion of Mononuclear Phagocytes to and Trafficking Through Endothelium in Vitro", Blood, vol. 92, pp. 4167-4177 (1998).
Randolph, et al., "The CD16(+) (FcγRIII(+)) Subset of Human Monocytes Preferentially Becomes Migratory Dendritic Cells in a Model Tissue Setting", J. Exp. Med., vol. 196, No. 4, pp. 517-527 (2002).

Razanajaona, et al., In Vitro Triggering of Somatic Mutation in Human Naïve B Cells, The Journal of Immunology, vol. 159, pp. 3347-3353 (1997).

Regnier, et al., "Integration of Langerhans Cells into a Pigmented Reconstructed Human Epidermis", The Journal of Investigative Dermatology, vol. 109, No. 4, pp. 510-512 (1997).

Robbiani, et al., "The Leukotriene C4 Transporter MRP1 Regulates CCL19 (MIP-3β, ELC)-Dependent Mobilization of Dendritic Cells to Lymph Nodes", Cell, vol. 103, pp. 757-768 (2000).

Roos et al. (2005) Expert Opin. Drug Metab. Toxicol. 1, 187-202.

Rot, "In Situ Binding Assay for Studying Chemokine Interactions with Endothelial Cells", Journal of Immunological Methods, vol. 273, pp. 63-71 (2003).

Ruco, et al., "Expression and Cell Distribution of the Intercellular Adhesion Molecule, Vascular Cell Adhesion Molecule, Endothelial Leukocyte Adhesion Molecule, and Endothelial Cell Adhesion Molecule (CD31) in Reactive Human Lymph Nodes and in Hodgkin's Disease", American Journal of Pathology, vol. 140, pp. 1337-1344 (1992).

Safarik, et al., "Use of Magnetic Techniques for the Isolation of Cells", Journal of Chromatography B, vol. 722, pp. 33-53 (1999).

Santini et al. (2000) J. Exp. Med. 191, 1777-1788.

Sarradell et al. (2003) Vet. Pathol., 40, 395-404.

Seguin, R. et al., "*Human Brain Endothelial Cells Supply Support for Monocyte Immunoregulartory Functions*," Journal of Neuroimmunology, (2003), 135(1-2), pp. 96-106.

Sieben, et al., "Comparison of Different Particles and Methods for Magnetic Isolation of Circulating Tumor Cells", Journal of Magnetism and Magnetic Materials, vol. 225, pp. 175-179 (2001).

Simmingskoeld et al., Scand. J. Immunol. 7:233-238 (1978).

Skibinski, et al., "Enhancement of Terminal B Lymphocyte Differentiation in Vitro by Fibroblast-Like Stromal Cells from Human Spleen", Eur. J. Immunol., vol. 28, pp. 3940-3948 (1998).

Skibinski, et al., "The Role of Hepatocyte Growth Factor and Its Receptor c-met in Interactions Between Lymphocytes and Stromal Cells in Secondary Human Lymphoid Organs", Immunology, vol. 102, pp. 506-514 (2001).

Soderberg, O. et al., "*The Human Follicular Dendritic Cell Line FDC-1 Binds Immune Complexes and Promotes Somatic Hypermutation*," Blood, (2001), 98(11 part 2), pp. 40b.

Sprent, et al., "Antigen-Induced Selective Recruitment of Circulating Lymphocytes", Cellular Immunology, vol. 2, pp. 171-181 (1971).

Stoll, et al., "Dynamic Imaging of T Cell-Dendritic Cell Interactions in Lymph Nodes", Science, vol. 296, pp. 1873-1876 (2002).

Stuart, et al., "The Human Reticular Cell: Morphology and Cytochemistry", J. Pathol, vol. 103, pp. 41-47 (1971).

Suematsu, et al., "Generation of a Synthetic Lymphoid Tissue-Like Organoid in Mice", Nature Biotechnology, vol. 22, No. 12, pp. 1539-1545 (Dec. 2004).

Tan et al. (2005) J. Leuk. Biol. 78, 319-324.

Tarte et al., Leukemia, vol. 14, 2000, abstract p. 2182.

Tew et al. (2001) Trends Immunol. 22, 361-367.

Tew, J. G. et al., "*Follicular Dendritic Cells As Accessory Cells*," Immunological Reviews, (1990), No. 117, pp. 185-211.

Tew, J.G. et al., "*Follicular Dendritic Cells and Presentation of Antigen and Costimulatory Signals to B Cells*," Immunological Reviews (1997), vol. 156, pp. 39-52.

Thompson, H.G. et al., "*A Three-dimensional in vitro Model of Angiogenesis in the Airway Mucosa*," Pulmonary Pharmacology & Therapeutics (2007), vol. 20, pp. 141-148.

Toyama, et al., "Memory B Cells Without Somatic Hypermutation are Generated from Bcl 6 Deficient B Cells", Immunity, vol. 17, pp. 329-339 (2002).

Transwell® Permeable Supports Selection and Use Guide, Corning Corp., pp. 1-12 (2009).

Tsunoda, R. et al., "*Follicular Dendritic Cells In Vitro Modulate the Expression of Fas and Bcl-2 on Germinal Center B Cells*," Cell and Tissue Research, (2000), 299(3), pp. 395-402.

Tsunoda, R. et al., "*Human Follicular Dendritic Cells In Vitro and Follicular Dendritic-Cell-Like Cells*," Cell and Tissue Research, (1997), 288(2), pp. 381-389.

Van Den Berg, et al., "Localization of β 1 Integrins and Their Extracellular Ligands in Human Lymphoid Tissues", American Journal of Pathology, vol. 143, pp. 1098-1110 (1993).

Weppler et al., Modulation of Endotoxin-Induced Neutrophil Transendothelial Migration by Alveolar Epithelium in a Defined Bilayer Model, Experimental Lung Research 32:10, 455-482 (2006).

West, et al., "Polymeric Biomaterials with Degradation Sites for Proteases Involved in Cell Migration", Macromolecules, vol. 32, pp. 241-244 (1999).

Wu et al. (2008) J. Immunol. 180, 281-290.

Wu, Y. et al., "*Influence of Follicular Dendritic Cells and Primed T Cells on Somatic Hypermutation in In Vitro Germinal Centers*," Journal of Immunology, (2006), 176(suppl. S), pp. S235-S236.

Zhang, S. et al., "*Growth Factors Secreted by Bronchial Epithelial Cells Control Myofibroblast Proliferation: An in vitro Co-culture Model of Airway Remodeling in Asthma*," Laboratory Investigation (1999), vol. 79, No. 4, pp. 395-405.

International Search Report—PCT/US2007/083795, 2007.
International Search Report—PCT/US2008/056720, 2008.
International Search Report—PCT/US08/70107a, 2008.
International Search Report—PCT/US06/048959, 2006.
International Search Report—PCT/US07/014826, 2006.
International Search Report—PCT/US08/69172, 2008.
International Search Report—PCT/US07/013745, 2007.
International Search Report—PCT/US05/14444, 2005.
International Search Report—PCT/US06/43563, 2006.
International Search Report—PCT/US06/43712, 2006.
International Search Report—PCT/US07/006532, 2007.
International Search Report—PCT/US07/006571, 2007.
International Search Report—PCT/US07/013871, 2007.
International Search Report—PCT/US06/049128, 2006.
International Search Report—PCT/US08/70107b, 2008.

Dynal (Norway): http://www.invitrogen.com/, 2010.

Agowa GmbH (Germany): http://agowade/contentsframes/magneticseparation/particle.html, 2010.

http://www.xcyte.com, 2010.

Protocol for anti-CD3 Activation of T-Cells from E-Bioscience (San Diego, CA): http://www.ebioscience..com/ebioscience/appls/AC145.htm, 2010.

Takeuchi et al., CCL21 Chemokine Regulates Chemokine Receptor CCR7 Bearing Malignant Melanoma Cells, Clin. Cancer Res. 10:2351-2358 (2004).

Katakai et al., Lymph Node Fibroblastic Reticular Cells Construct the Stromal Reticulum via Contact with Lymphocytes, J. Exp. Med. 200(6):783-795 (2004).

Caux et al., Functional CD40 on B Lymphocytes and Dendritic Cells, Res. Immunol. 145:235-239 (1994).

Inaba et al., Clustering of Dendritic Cells, Helper T Lymphocytes, and Histocompatible B Cells During Primary Antibody Response In vitro, J. Exp. Med. 160:858-876 (1984).

Grouard et al., Regulation of Human B Cell Activation by Follicular Dendritic Cell and T Cell Signals, Curr. Topic Microbiol. Immunol. 201:105-117 (1995).

Warren, W., The Front-End of Vaccine Manufacturing: Getting Good Candidates from the Get-Go. Workshop on Science and Technology in North American Rapid Vaccine Manufacturing, Jan. 26, 2007.

Hashimoto, K., et al., Direct Observation and Analysis of Spatiotemporal Dynamics of Individual Living Monocyte During Transendothelial Migration. Atherosclerosis 177(1):19-27 (Nov. 2004).

Hashimoto, K., et al., Direct Observation and Analysis of Spatiotemporal Dynamics of Individual Living Monocyte During Transendothelial Migration. Collection of Papers from 16th Bioengineering Conference, Jan. 21, 2004, pp. 13-14.

Higbee, R., et al., An Immunologic Model for Rapid Vaccine Assessment—A Clinical Trial in a Test Tube. ALTA 37, Suppl. 1, 19-27 (2009).

* cited by examiner

Improved tetanus toxoid-specific antibody
responses in T and B cell
co-culture LTE, as compared to PBMC cultures

METHOD FOR DETERMINING THE IMMUNOGENICITY OF AN ANTIGEN

CROSS REFERENCE TO RELATED CASES

This application is a divisional of U.S. application Ser. No. 11/594,172, filed Nov. 8, 2006, which is continuation-in-part of U.S. application Ser. No. 11/453,046, filed Jun. 15, 2006, which is a continuation-in-part of U.S. application Ser. No. 11/116,234, filed Apr. 28, 2005, which claims the benefit of U.S. Provisional Application Ser. Nos. 60/565,846, filed Apr. 28, 2004, and 60/643,175, filed Jan. 13, 2005. This application also claims the benefit of priority of International Application No. PCT/US05/014444, filed Apr. 28, 2005. Each of these applications is hereby incorporated by reference in their entirety

STATEMENT REGARDING FEDERALLY SPONSORED RESEARCH

This invention was made with government support under contract number NBCHC060058, awarded by the Defense Advanced Research Projects Agency, issued by the U.S. Army Medical Research Acquisition Activity, and administered by the U.S. Department of the Interior-National Business Center. The government has certain rights in the invention.

BACKGROUND OF THE INVENTION

1. Field of the Invention

The present invention is directed to a method for constructing an integrated artificial human tissue construct system and, in particular, construction of an integrated human immune system for in vitro testing of vaccines, adjuvants, immunotherapy candidates, cosmetics, drugs, biologics, and other chemicals. The artificial immune system of the present invention is useful for assessing the interaction of substances with the immune system, and thus can be used to accelerate and improve the accuracy and predictability of, for example, vaccine, drug, biologic, immunotherapy, cosmetic, and chemical development.

2. Background of the Technology

Despite the advent and promise of recent technologies, including combinatorial chemistry, high-throughput screening, genomics, and proteomics, the number of new drugs and vaccines reaching the market has not increased. In fact, the attrition rate within drug discovery programs exceeds 90%.

The introduction of these new (and expensive) technologies has not reduced the lost opportunity costs associated with immunotherapy development; rather, these costs have increased. Indeed, it is now estimated that almost $1 billion is required to bring a new drug to the market.

The development and biological testing of human vaccines has traditionally relied on small animal models (e.g., mouse and rabbit models) and then non-human primate models. However, such small animal models are expensive and non-human primate models are both expensive and precious. Furthermore, there are many issues regarding the value of such animal studies in predicting outcomes in human studies.

A major problem remains the translation from test systems to human immunology. Successful transfer between traditional testing systems and human biology requires an intricate understanding of disease pathogenesis and immunological responses at all levels. Given worldwide health problems caused by known and emerging infectious agents and even potential biological warfare pathogens, it is time for a fresh approach to understanding disease pathogenesis, the development and rapid testing of vaccines, and insights gathered from such work.

The body's distributed immune system can be roughly divided into four distinct compartments: tissues and blood, mucosal tissues, body cavities, and skin. Because of ease of study, most is known about the tissue and blood compartment and its lymphoid tissues, the spleen and lymph nodes.

The mammalian immune system uses two general adaptive mechanisms to protect the body against environmental pathogens. When a pathogen-derived molecule is encountered, the immune response becomes activated to ensure protection against that pathogenic organism.

The first immune system mechanism is the non-specific (or innate) inflammatory response. The innate immune system appears to recognize specific molecules that are present on pathogens but not within the body itself.

The second immune system mechanism is the specific or acquired (or adaptive) immune response. Innate responses are fundamentally the same for each injury or infection; in contrast, acquired responses are custom-tailored to the pathogen in question. The acquired immune system evolves a specific immunoglobulin (antibody) response to many different molecules, or antigens, derived from the pathogen. In addition, a large repertoire of T cell receptors (TCR) is sampled for their ability to bind processed peptides from the antigens that are bound by major histocompatibility complex (MHC) class I and II proteins on the surface of antigen-presenting cells (APCs), such as dendritic cells (DCs).

Acquired immunity is mediated by specialized immune cells called B and T lymphocytes (or simply B and T cells). Acquired immunity has specific memory for specific antigens; repeated exposure to the same antigen increases the memory response, which increases the level of induced protection against that particular pathogen.

B cells produce and mediate their functions through the actions of antibodies. B cell-dependent immune responses are referred to as "humoral immunity" because antibodies are found in body fluids.

T cell-dependent immune responses are referred to as "cell-mediated immunity," because effector activities are mediated directly by the local actions of effector T cells. The local actions of effector T cells are amplified through synergistic interactions between T cells and secondary effector cells, such as activated macrophages. The result is that the pathogen is killed and prevented from causing diseases.

The functional element of a mammalian lymph node is the follicle, which develops a germinal center (GC) when stimulated by an antigen. The GC is an active area within a lymph node, where important interactions occur in the development of an effective humoral immune response. Upon antigen stimulation, follicles are replicated and an active human lymph node may have dozens of active follicles, with functioning GCs. Interactions between B cells, T cells, and FDCs take place in GCs.

Various studies of GCs in vivo indicate that the many important events occur there, including immunoglobulin (Ig) class switching, rapid B cell proliferation (GC dark zone), production of B memory cells, accumulation of select populations of antigen-specific T cells and B cells, hypermutation, selection of somatically mutated B cells with high affinity receptors, apoptosis of low affinity B cells, affinity maturation, induction of secondary antibody responses, and regulation of serum immunoglobulin G (IgG) with high affinity antibodies. Similarly, data from in vitro GC models indicate that FDCs are involved in stimulating B cell proliferation with mitogens and it can also be demonstrated with antigen (Ag), promoting production of antibodies including recall antibody responses, producing chemokines that attract B cells and certain populations of T cells, and blocking apoptosis of B cells.

Similar to pathogens, vaccines function by initiating an innate immune response at the vaccination site and activating antigen-specific T and B cells that can give rise to long term memory cells in secondary lymphoid tissues. The precise interactions of the vaccine with cells at the vaccination site and with T and B cells of the lymphoid tissues are important to the ultimate success of the vaccine.

Almost all vaccines to infectious organisms were and continue to be developed through the classical approach of generating an attenuated or inactivated pathogen as the vaccine itself. This approach, however, fails to take advantage of the recent explosion in our mechanistic understanding of immunity. Rather, it remains an empirical approach that consists of making variants of the pathogen and testing them for efficacy in non-human animal models.

Advances in the design, creation and testing of more sophisticated vaccines have been stalled for several reasons. First, only a small number of vaccines can be tested in humans, because, understandably, there is little societal tolerance for harmful side effects in healthy people, especially children, exposed to experimental vaccines. With the exception of cancer vaccine trials, this greatly limits the innovation that can be allowed in the real world of human clinical trials. Second, it remains challenging to predict which immunodominant epitopes are optimal for induction of effective $CD4^+$ and $CD8^+$ T cell responses and neutralizing B cell responses. Third, small animal testing, followed by primate trials, has been the mainstay of vaccine development; such approaches are limited by intrinsic differences between human and non-human species, and ethical and cost considerations that restrict the use of non-human primates. Consequently, there has been a slow translation of basic knowledge to the clinic, but equally important, a slow advance in the understanding of human immunity in vivo.

The artificial immune system (AIS) of the present invention can be used to address this inability to test many novel vaccines in human trials by instead using human tissues and cells in vitro. The AIS enables rapid vaccine assessment in an in vitro model of human immunity. The AIS provides an additional model for testing vaccines in addition to the currently used animal models.

Attempts have been made in modulating the immune system. See, for example, U.S. Pat. No. 6,835,550 B1, U.S. Pat. No. 5,008,116, WO 2004/101773 A1, Suematsu et al., (*Nat Biotechnol*, 22, 1539-1545, (2004)) and U.S. Patent Application No. 2003/0109042.

Nevertheless, none of these publications describe or suggest an artificial (ex vivo) human cell-based, immune-responsive system comprising a vaccination site (VS) and a lymphoid tissue equivalent (LTE). The present invention comprises such a system and its use in assessing the interaction of substances with the immune system.

SUMMARY OF THE INVENTION

The present invention is directed to artificial immune systems comprising cell cultures of B cells, T cells and antigen-primed dendritic cells.

The present invention is also directed to methods for detecting an immune response to an antigen using the cell cultures of the present invention.

DETAILED DESCRIPTION OF THE INVENTION

Figure 1:
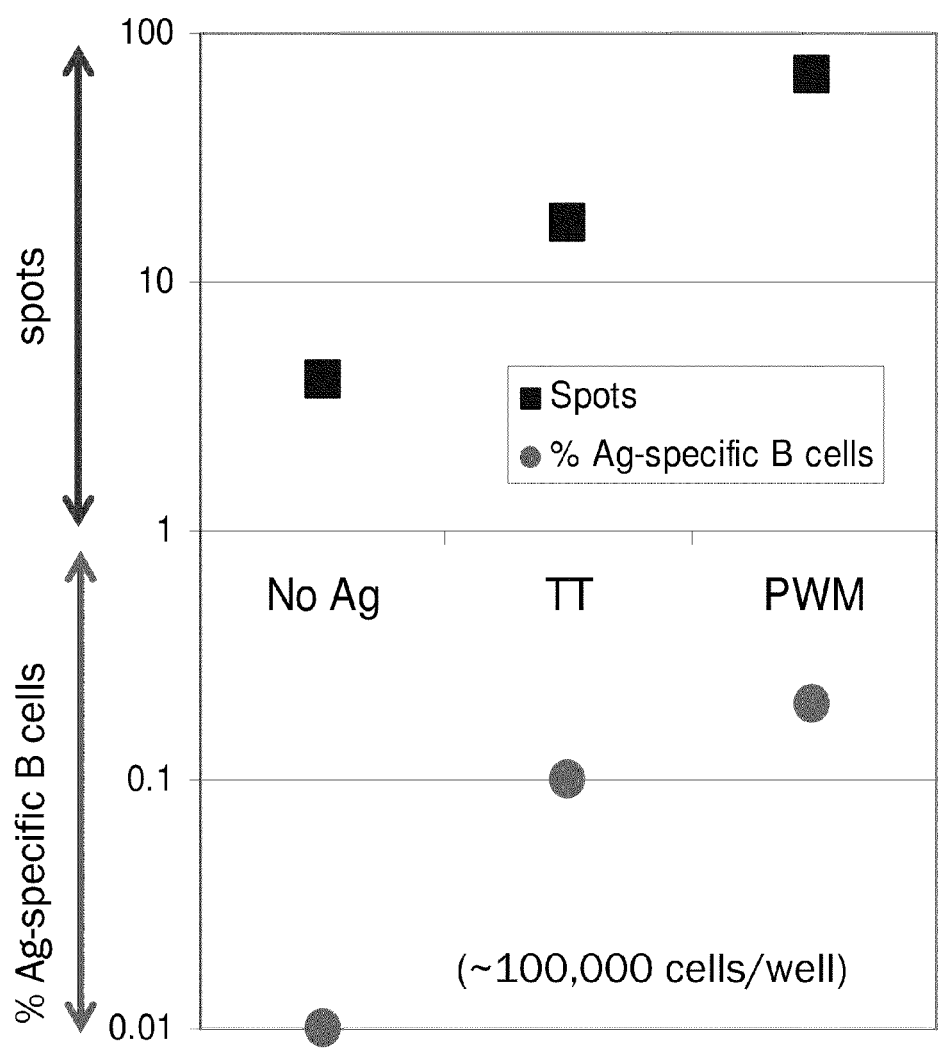
FIG. 1: Shows the detection of tetanus-specific antibody responses by ELISPOT and determination of the percentage of antigen-specific B cells using a 2D T and B cell co-culture.

The present invention concerns the development of accurate, predictive in vitro models to accelerate vaccine testing, allow collection of more informative data that will aid in redesigning and optimizing vaccine formulations before animal or clinical trials, and raise the probability that a vaccine candidate will be successful in human trials. More specifically, the present invention comprises controlling the nature and state of the cells in the lymphoid tissue equivalent (LTE, artificial lymph node) of the artificial immune system (AIS).

The AIS can be used to test vaccines and other pharmaceuticals for immune reactivity in a manner that is more predictive than animal experiments. Consequently, it can provide valuable pre-clinical data earlier in the research and development process. Antigenic molecules introduced to the AIS are acquired by dendritic cells (DCs) at the vaccination site (VS). The DCs are then transferred to the lymphoid tissue equivalent (LTE), where they present the antigen to T cells, activating their immune function. Activated helper T cells co-stimulate B cells to induce antibody production, while activated cytotoxic T cells lyse antigen-bearing cells. Solubilized antigen(s) can also be introduced into the LTE to directly activate B cells for subsequent antibody production.

While a number of published reports have demonstrated antigen-specific B cell responses (to *C. albicans*, TT, and other antigens) in vitro, these results are typically achieved by stimulating and restimulating cultures of whole PBMCs with antigen and exogenous factors to boost B cell proliferation and/or activation.

The present invention comprises the detection of antibody responses using defined cultures of B cells, T cells, and DCs and optionally follicular dendritic cells (FDCs), in 2-dimensional construct assay. The presence of secondary cells provides a more physiological environment for B cell activation and differentiation, such that artificial factors in the cultures are not necessary to detect specific antibody responses. In an embodiment of the present invention, the LTE comprises allogeneic T cells. In another embodiment, the LTE comprises autologous T cells.

Using embodiments of the present invention, we have generated antigen-specific B cell responses using a 2-dimensional (2D) co-culture system comprising T cells, B cells, and antigen-pulsed DCs. In the examples, responses were generated against tetanus toxoid (TT) and a whole protein extract of *Candida albicans* (*C. albicans*). The results from these examples show that culturing human T and B cells together in vitro at a ~1:1 ratio, versus the ratio of T and B cells naturally found in the blood, gave stronger antigen responses, by both analysis of activation and proliferation (flow cytometry) and antibody production (ELISPOT). Although the preferred ratio of T cells:B cells is ~1:1, the ratio of T cells:B cells can range from ~1:10 to ~10:1. In the cultures of the examples, "T cells" included both $CD4^+$ and $CD8^+$ T cells. In peripheral blood, the T (total T cells):B cell ratio is ~7:1. In the lymph node, the T (total T cells):B cell ratio is ~1:1.6. In the germinal center, the T cell:B cell ratio is ~1:8, and there, the T cells are primarily $CD4^+$ T cells.

In the results of the experiments shown, engineered serum-free media (X-VIVO) was used, though we have also used serum (e.g., human, bovine) in other experiments (data not shown). Dendritic cells (DCs) were generated from CD14- purified monocytes that were cultured for ~7 days in X-VIVO 15 media, supplemented with GM-CSF (~100 ng/ml) and IL-4 (~25 ng/ml). The cytokine-derived DCs were pulsed with antigen or vaccine and then cocultured with T cells. After adding the antigen-prepulsed dendritic cells to the T cell culture, B cells primed with the same antigen used to prime the DCs are added to the cell culture. After adding the antigen-primed B cells to the cell culture, further soluble antigen can also be added. For PBMC cultures, either the antigen was added to the assay, or antigen-pulsed DCs were added to the assay. In FIGS. 1 to 9, antigen-pulsed DCs were added to the co-culture of T and B cells, while soluble antigen was added to the PBMC cultures. FIG. 9 shows a comparison of the co-culture to PBMCs, with antigen-pulsed DCs added to both systems.

Antibodies specific for the antigen of interest can be isolated from the resulting cell cultures of the present invention. Such antibodies can be used for a variety of purposes, including in therapeutic and diagnostic methods.

In addition, antigen-specific B cells can be isolated, cloned and immortalized from the cell cultures of the present invention, and can also be used in therapeutic and diagnostic methods.

Alternatively, all of the antibody-producing B cells are collected en masse (without isolating/cloning individual B cells) for immortalizing and producing a therapeutic.

Thus, the present invention also encompasses methods of producing a therapeutic comprising antibodies or antibody-producing B cells in combination with a pharmaceutically acceptable carrier.

EXAMPLES

These experiments provide a direct comparison of PBMCs versus a co-culture of negatively selected T and B cells that were plated at a ~1:1 ratio in—in these examples—a 96-well, round bottom plate. All assays were harvested on day 7 of in vitro culture. All experiments were analyzed by ELISPOT for antibody production and by flow cytometry for proliferation, as determined by loss of CFSE. In the ELISPOT assays because there were different ratios of T and B cells in the PBMC culture compared with the TB-2D cultures, there were fewer B cells plated into the ELISPOT wells. However, in the experiment in FIG. 4, the numbers of B cells used in the ELISPOT experiments for both the PBMC and co-culture assays were approximately equal. We determined the approximate number of B cells in the ELISPOT wells by flow cytometry to enable comparisons.

These results show that culturing human T and B cells together in vitro at a ~1:1 ratio compared to the ratio of T and B cells naturally found in the blood give stronger antigen responses, by both analysis of activation and proliferation (flow cytometry) and antibody production (ELISPOT). The results also show that co-culturing T cells and antigen-primed dendritic cells, and subsequently adding antigen-primed B cells, also gives stronger antigen responses, as indicated by antibody production (ELISPOT).

Example 1

B and T cell co-culture with tetanus toxoid, showing the ability to detect tetanus-specific antibody responses.

Example 2a

Figure 4:
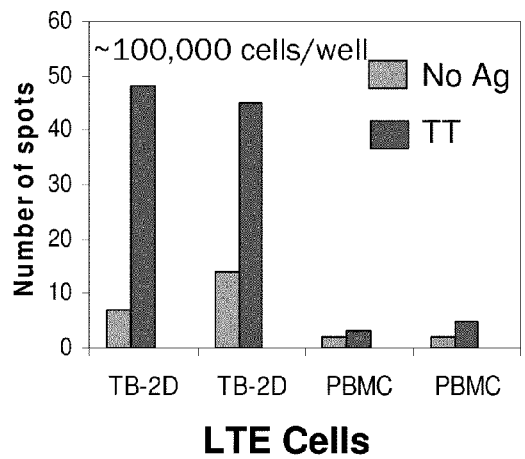
FIG. 4: Depicts tetanus toxoid-specific ELISPOT comparing PBMC to 2D T and B cell co-culture for the same cell donor shown in FIGS. 2 and 3.
Figure 4:
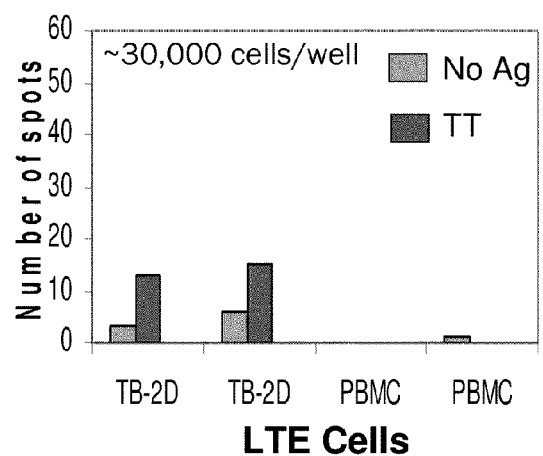

PBMC versus co-culture, using a tetanus toxoid antigen. Even though similar B cell proliferation responses were seen in PBMC and 2D T and B cell co-cultures (FIGS. 2, 3), an improved tetanus toxoid-specific antibody response was observed in a T and B cell co-culture LTE, as compared with PBMC cultures (FIG. 4).

Example 2b

PBMC versus co-culture, using *Candida albicans* antigens. FIG. 9 shows *C. albicans*-specific ELISPOT data, comparing TB-2D to PBMCs. In this experiment, DCs were pulsed with TT antigen only, but the ELISPOT was conducted on both TT- and *C. albicans*-coated plates.

Example 2c

Figure 10:
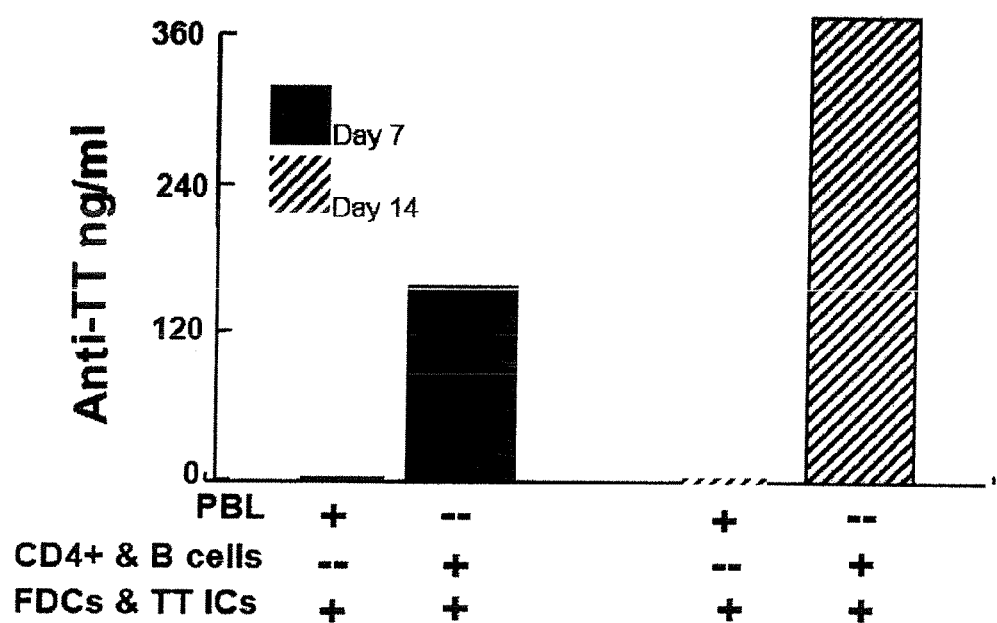
FIG. 10: Depicts antibody responses when some of the leukocytes are removed.

PBMC versus co-culture (FIG. 10). In this example we addressed the question of what happens if we take cells from an apparent "non-responder" and use only the GC cells from the leukocytes. Note the response when some of the leukocytes are removed (FIG. 10); non-responders in vitro now show an antibody response.

Here, we used human $CD4^+$ T and B cells with FDCs and formed GCs in vitro and then examined whether IgG production could be obtained against a recall antigen. Specifically, we used tetanus toxoid (TT) in these experiments and isolated human B cells and $CD4^+$ T cells from peripheral blood.

We observed IgG recall responses using only the T cells, B cells, and FDCs that are typically found in GCs. In contrast, in the presence of PBL cells not normally in found in GCs, no antibody response was detectible in cells from some donors. These results show that removing (not including) other cells, such NK cells, monocytes, and $CD8^+$ T cells, improved the IgG response.

Example 3

Figure 5A:
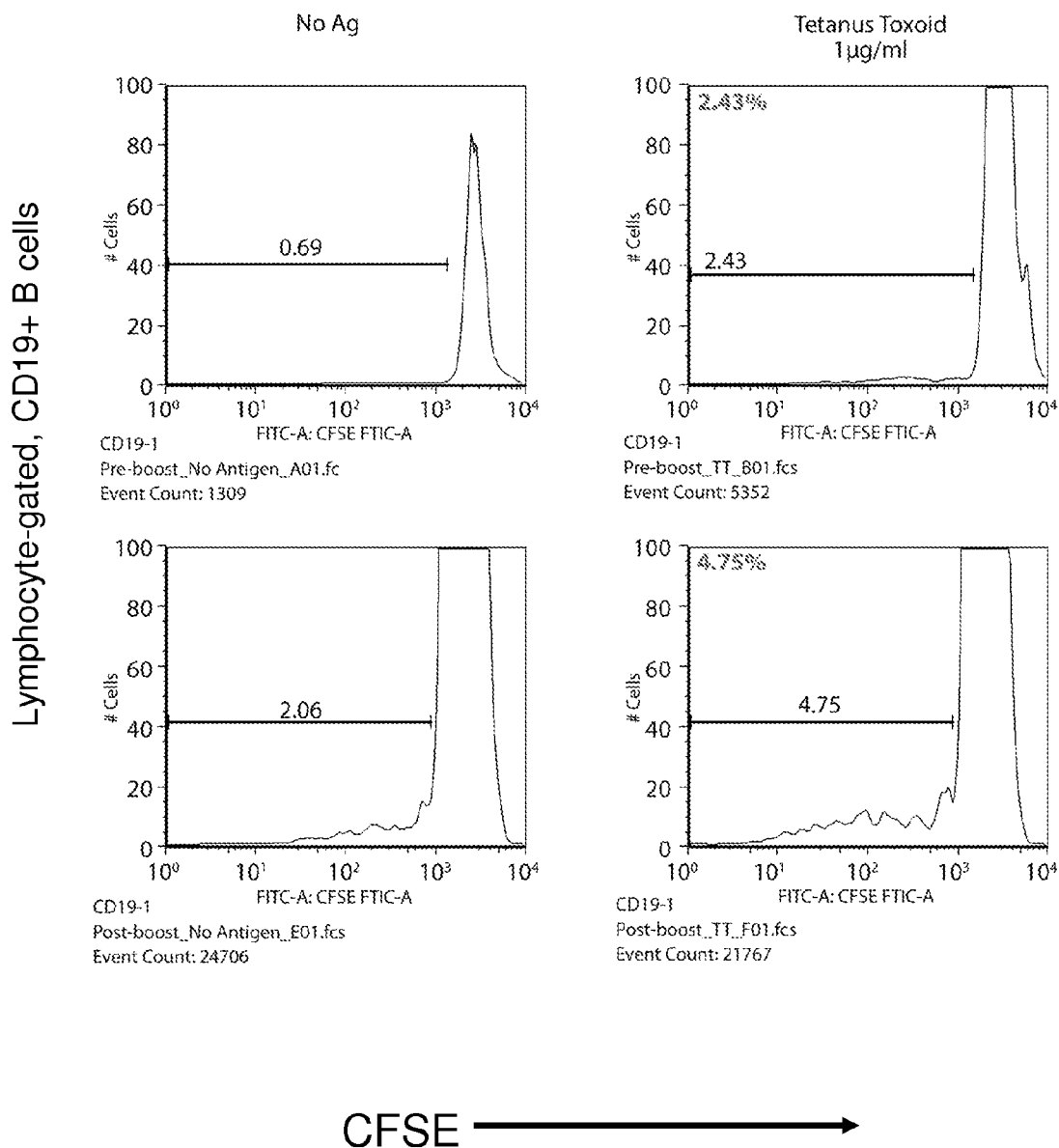
FIG. 5: Shows an in vitro system representative of the physiological state promotes stronger B cell proliferative and tetanus toxoid-specific antibody responses, using a 2D co-culture of T and B cells and TT-pulsed DCs.
Figure 5B:
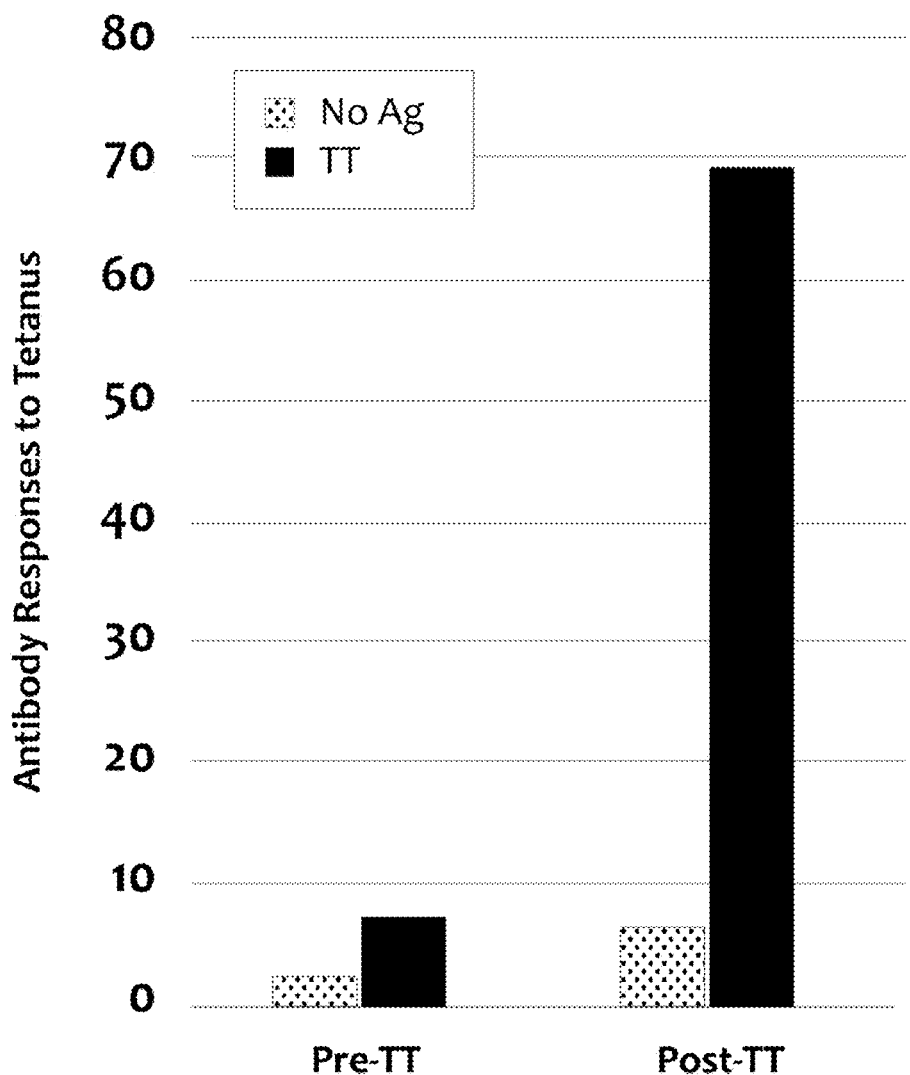
Figure 6:
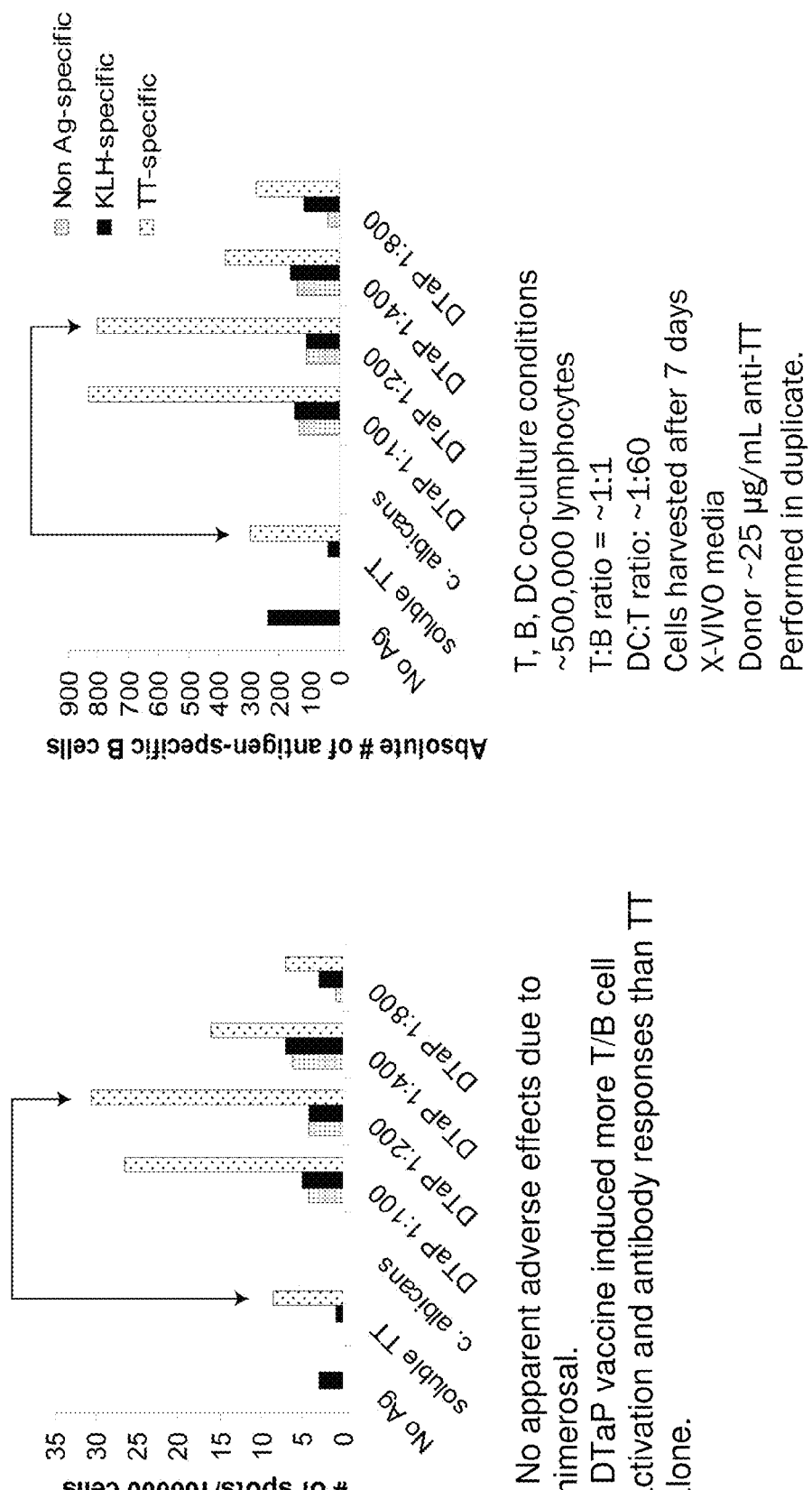
FIG. 6: Depicts tetanus-specific antibody responses to a DTaP (diphtheria and tetanus and acellular pertussis vaccine, adsorbed) vaccine and a simple tetanus toxoid Antigen, using a 2D co-culture of T and B cells and TT-pulsed DCs.
Figure 7:
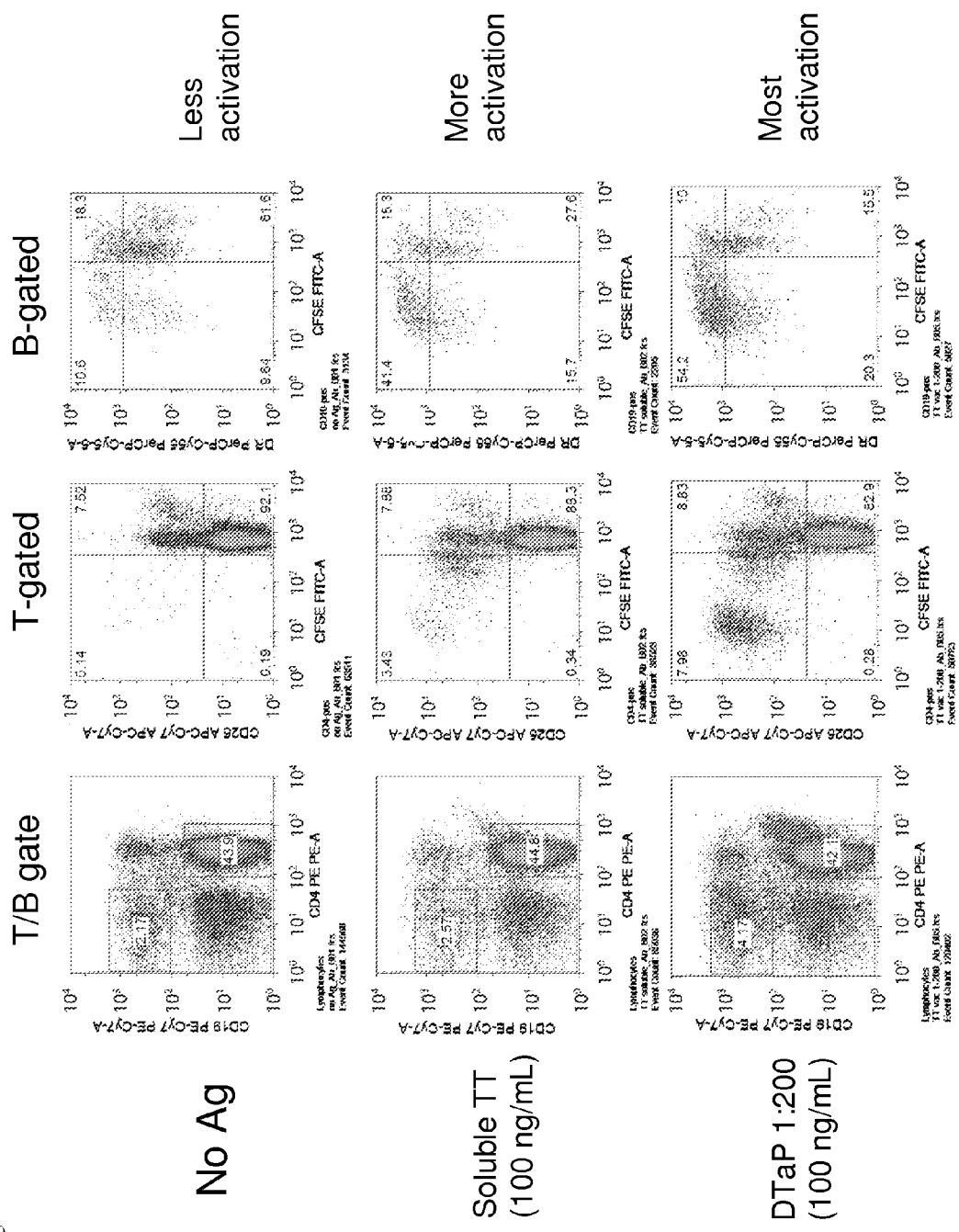
FIG. 7: Shows the influence of vaccine versus antigen in a lymphoid tissue equivalent (LTE) for the same cell donor shown in FIG. 6.

In vitro system representative of the physiological state promotes higher B cell proliferative and tetanus toxoid-specific antibody responses following tetanus vaccination (FIG. 5). The post tetanus toxoid experiment was conducted 5 weeks following vaccination. The tetanus antibody titer before vaccination was ~40 μg/mL; after vaccination it was ~300 μg/mL. T cells represent both $CD4^+$ and $CD8^+$ T cells. Peripheral blood has a T:B ratio of ~7:1 (total T cells). The lymph node has a T:B ratio of ~1:1.6 (total T cells). The germinal center has a T:B ratio of ~1:8 (primarily $CD4^+$ T cells).

Example 4

Use of a vaccine to elicit in vitro immune responses in a co-culture of T and B cells. DCs were pulsed with the vaccine or the tetanus toxoid antigen and were then added to the co-culture of T and B cells. Tripedia® (diphtheria and tetanus toxoids and acellular pertussis vaccine, adsorbed; DTaP), for intramuscular use, is a sterile preparation of diphtheria and tetanus toxoids adsorbed, with acellular pertussis vaccine in an isotonic sodium chloride solution containing thimerosal (preservative) and sodium phosphate (to control pH). After shaking, the vaccine is a homogeneous white suspension. Tripedia® vaccine is distributed by Aventis Pasteur Inc.

Example 5

To detect antigen-specific antibody responses, we developed an ELISPOT approach to quantify B cell responses (antigen specificity) on a per cell basis. In this example, T cells were cultured with B cells at a ~1:1 ratio, with cytokine-derived DCs included at a DC:T and B (total) cell ratio of ~1:60. Soluble TT (~1 μg/ml) or C. albicans (~10 μg/ml) was included for the entire 7-day culture, while other wells received pokeweed mitogen (PWM; a strong, non-specific lymphocyte stimulator) for the final 3 days of the culture.

On the seventh day, the lymphocytes were examined for marker expression and CFSE profiles by flow cytometry and the frequency of TT and C. albican-specific B cells was calculated by ELISPOT. Briefly, $\sim 30 \times 10^3$ total lymphocytes were plated in duplicate wells of an ELISPOT plate that had been pre-coated with TT, C. albicans, or anti-immunoglobulin (Ig, to gauge total antibody production).

The cells were then serially diluted five times at a ~1:3 ratio and PWM was added to all wells to trigger antibody production. The cells were then incubated for ~5 hr at 37° C. in a 5% $CO_2$ incubator and washed away. Plate-bound antibody was detected using techniques similar to those required for ELISA.

Figure 8A:
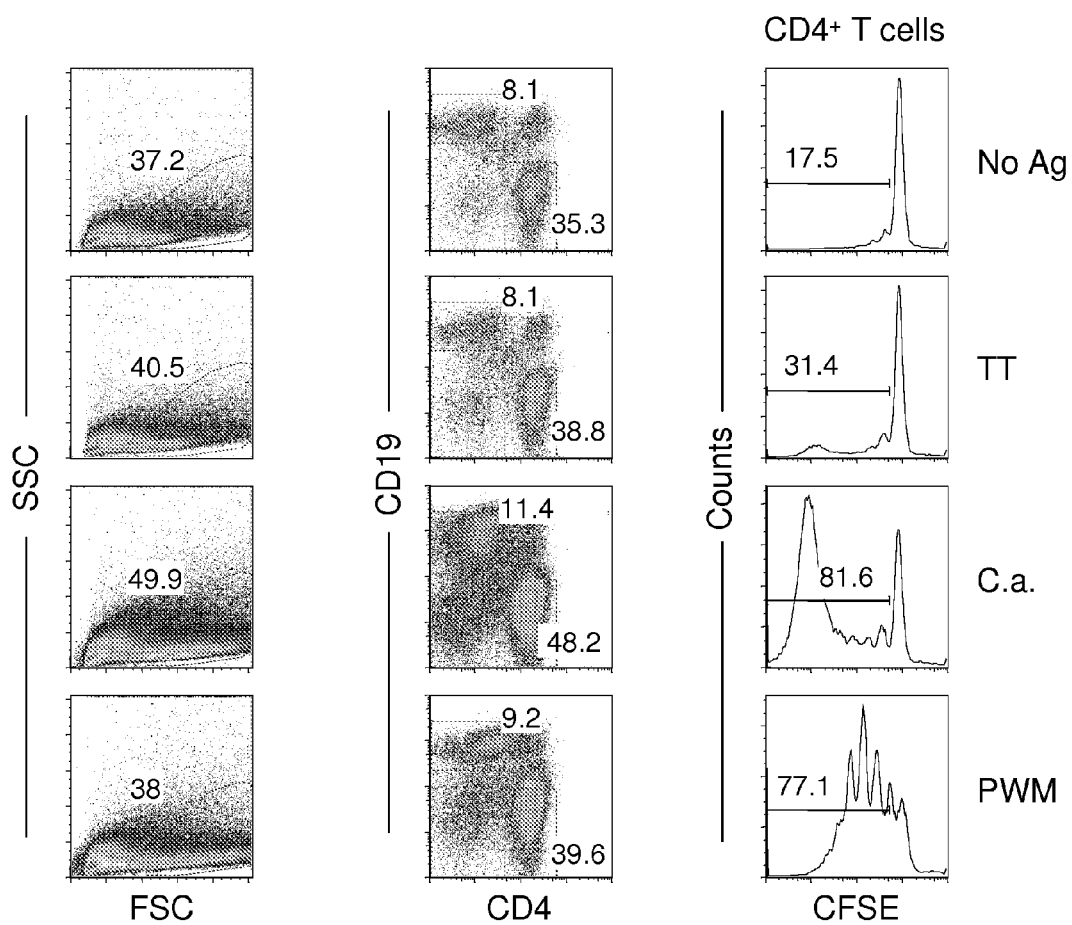
FIG. 8: Depicts Strong B cell and T cell proliferative responses seen against *C. albicans*, associated with potent activation (HLA-DR$^{high}$, CD86$^{high}$) of the dividing B cells using a 2D co-culture of T and B cells and TT-pulsed DCs.
Figure 8B:
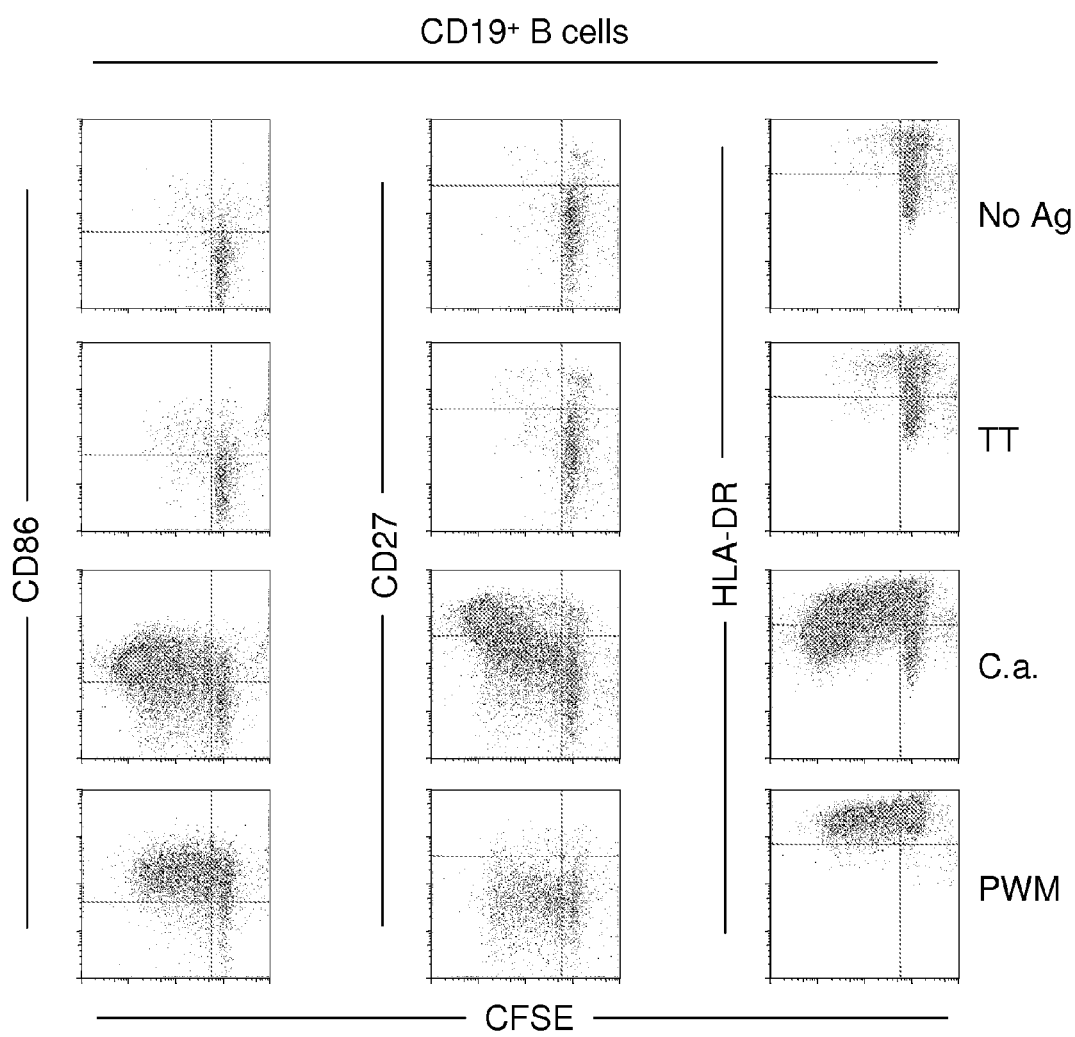
Figure 9:
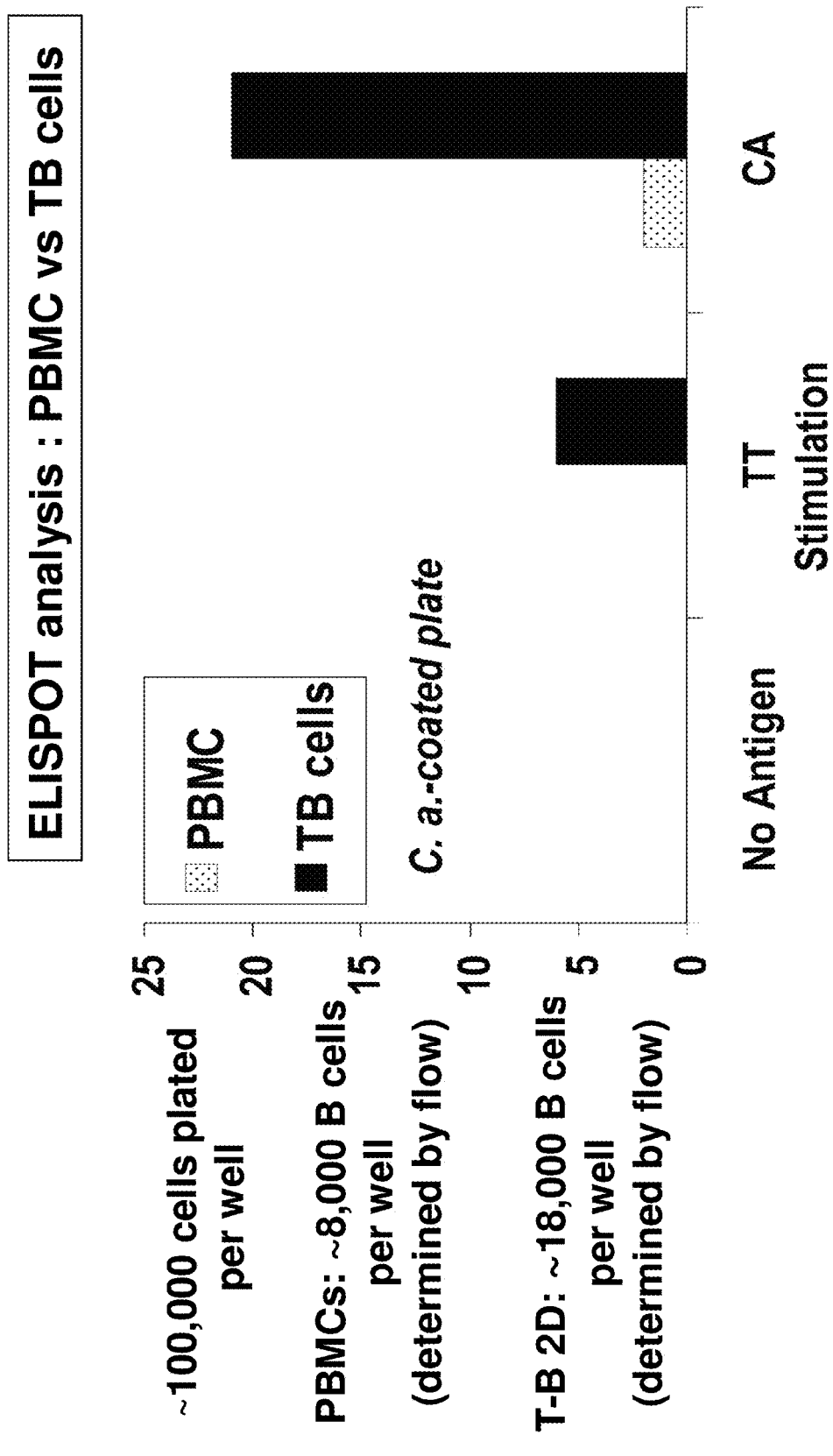
FIG. 9: Shows specificity of the *C. albican*-stimulated B cells demonstrated by ELIPSOT for the same donor in FIG. 8. *C. albicans*-specific ELISPOT data comparing compares the 2D co-culture of T and B cells with PBMCs.

The results in FIG. 8 demonstrate strong B cell and T cell proliferative responses against C. albicans, associated with potent activation ($HLA-DR^{high}$, $CD86^{high}$) of the dividing B cells. Furthermore, a subset of the most divided B cells appears to have acquired a memory phenotype, indicated by increased CD27 expression.

The lack of a robust response against TT was consistent with the weak serum TT titer for this donor (~4 μg/ml). As expected, PWM triggered potent T and B cell proliferative responses, though not as many divisions were seen as with specific antigen stimulation, likely because the cells were only cultured with the mitogen for 3 days.

Figure 2:
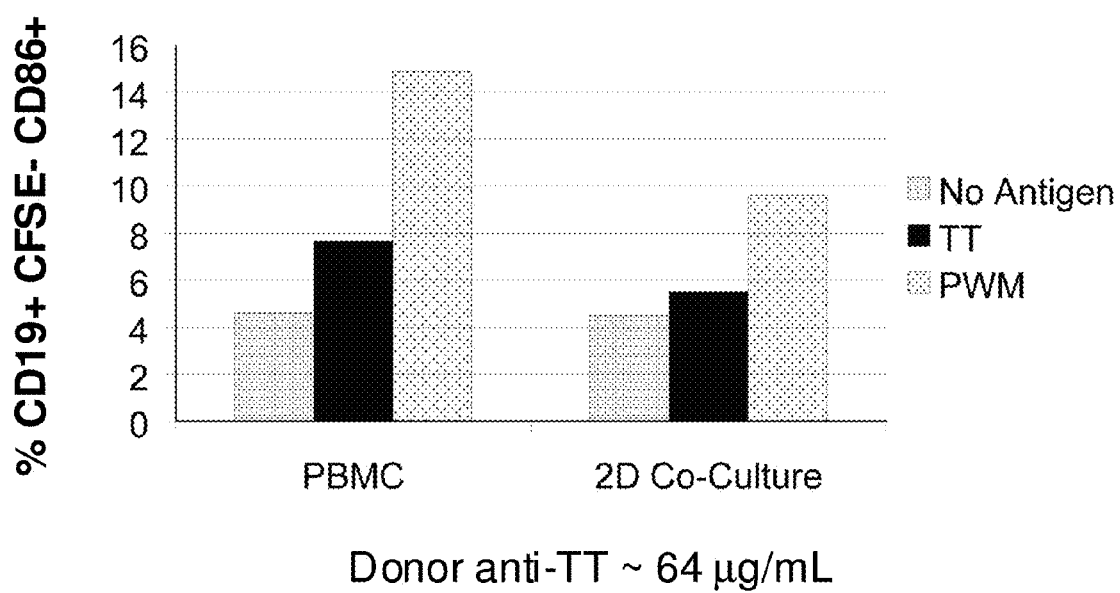
FIG. 2: Depicts tetanus toxoid: B cell proliferation and comparison between PBMC and 2D T and B cell co-culture.
Figure 3:
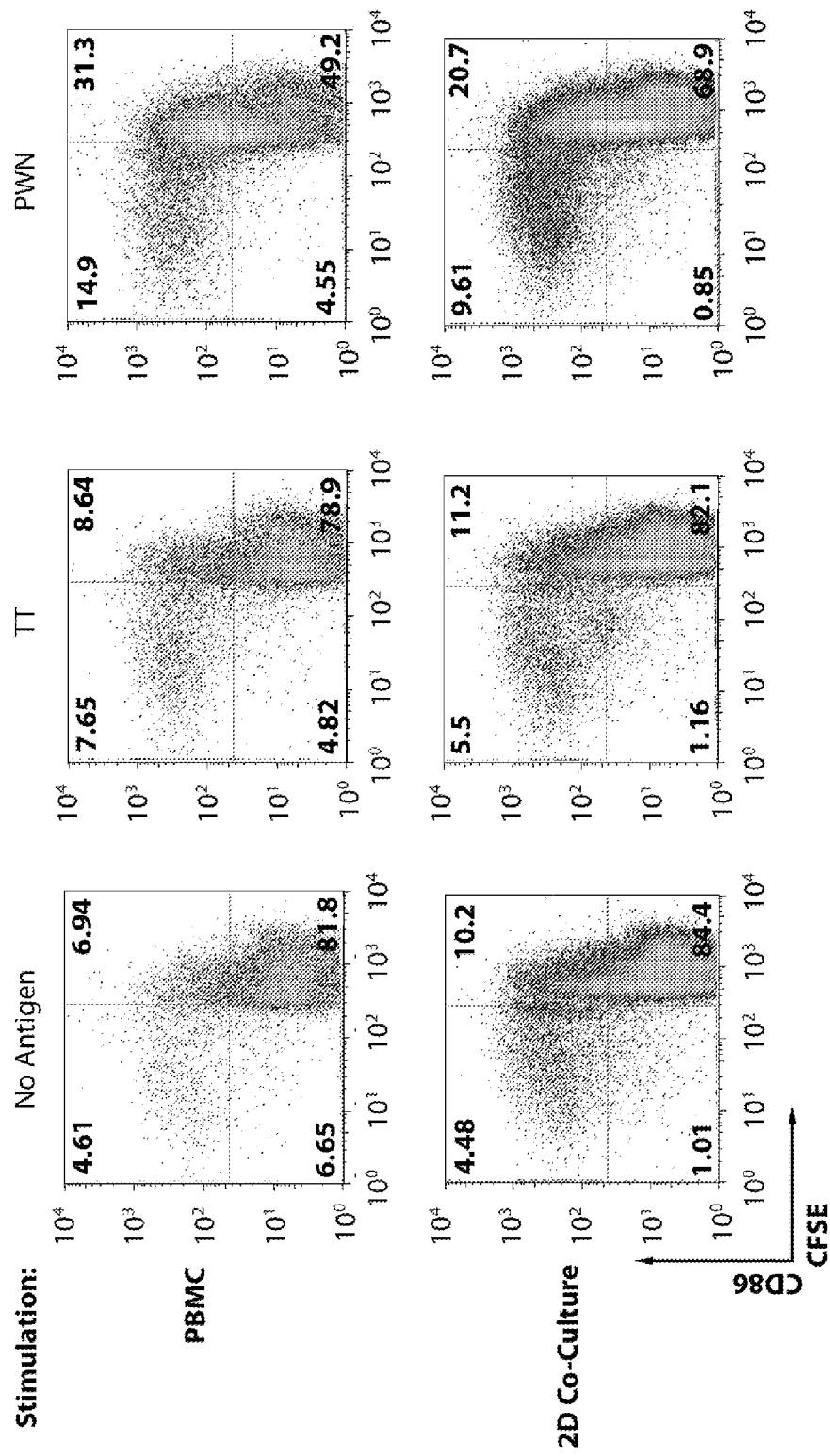
FIG. 3: Shows the flow cytometry data indicating B cell proliferation between PBMC and 2D T and B cell co-culture for the same cell donor shown in FIG. 2.

The specificity of the C. albicans-stimulated B cells was demonstrated by ELIPSOT (FIG. 2). This experiment suggests that a 1× stimulation with C. albicans did give rise to a small population of antibody-producing cells (~0.2% of total B cells) that was not detected in untreated cultures or those stimulated with TT (left and middle wells). This discrepancy between the frequency of proliferating cells and C. albicans-specific B cells detected by ELISPOT could be the result of several factors. A likely explanation is that we used a crude C. albicans whole antigen extract containing ~19% carbohydrates (by weight). While C. albicans polysaccharides are strong inducers of B cell responses, only protein antigen-specific responses would be detected in the ELISPOT assay.

Example 6

Tetanus-specific antibodies were detected in another ELISPOT experiment where the cell donor's serum anti-tetanus level was higher (63 μg/ml), and DCs were cultivated in XVIVO-15 medium. All other components, concentrations and ratios were left unchanged, except that of the number of cells deposited per ELISPOT well was increased; the higher number used was $\sim 1 \times 10^5$ cells/well.

In this experiment, both TT- and C. albicans-specific antibodies were observed (up to 48 and 33 spots per well, respectively), although a high level of non-specific response, especially in the presence of CCL21/anti-CD40 additives, did not allow a firm conclusion in favor of antigen-specific versus mitogenic activity.

Example 7

The specificity of the C. albicans-stimulated B cells was demonstrated by ELIPSOT (FIG. 9) for both PBMC and 2D co-culture of T and B cells with C. albicans-pulsed DCs added to both systems. This experiment indicates that even if the PBMC cultures have antigen-pulsed DCs added that the co-culture system shows a stronger antibody response, as determined by ELISPOT.

Example 8

Figure 11:
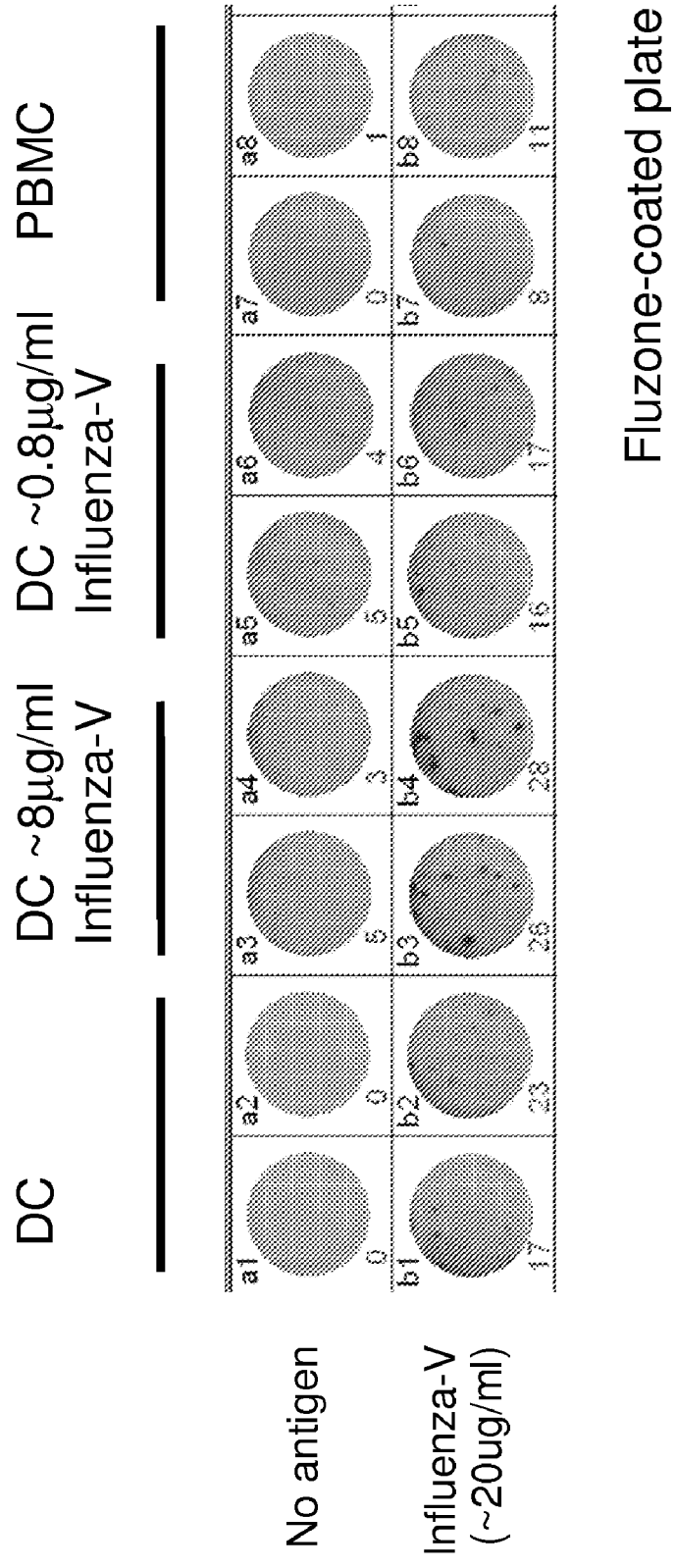
FIG. 11: Shows in vitro antigen-specific antibody response to influenza.
Figure 12:
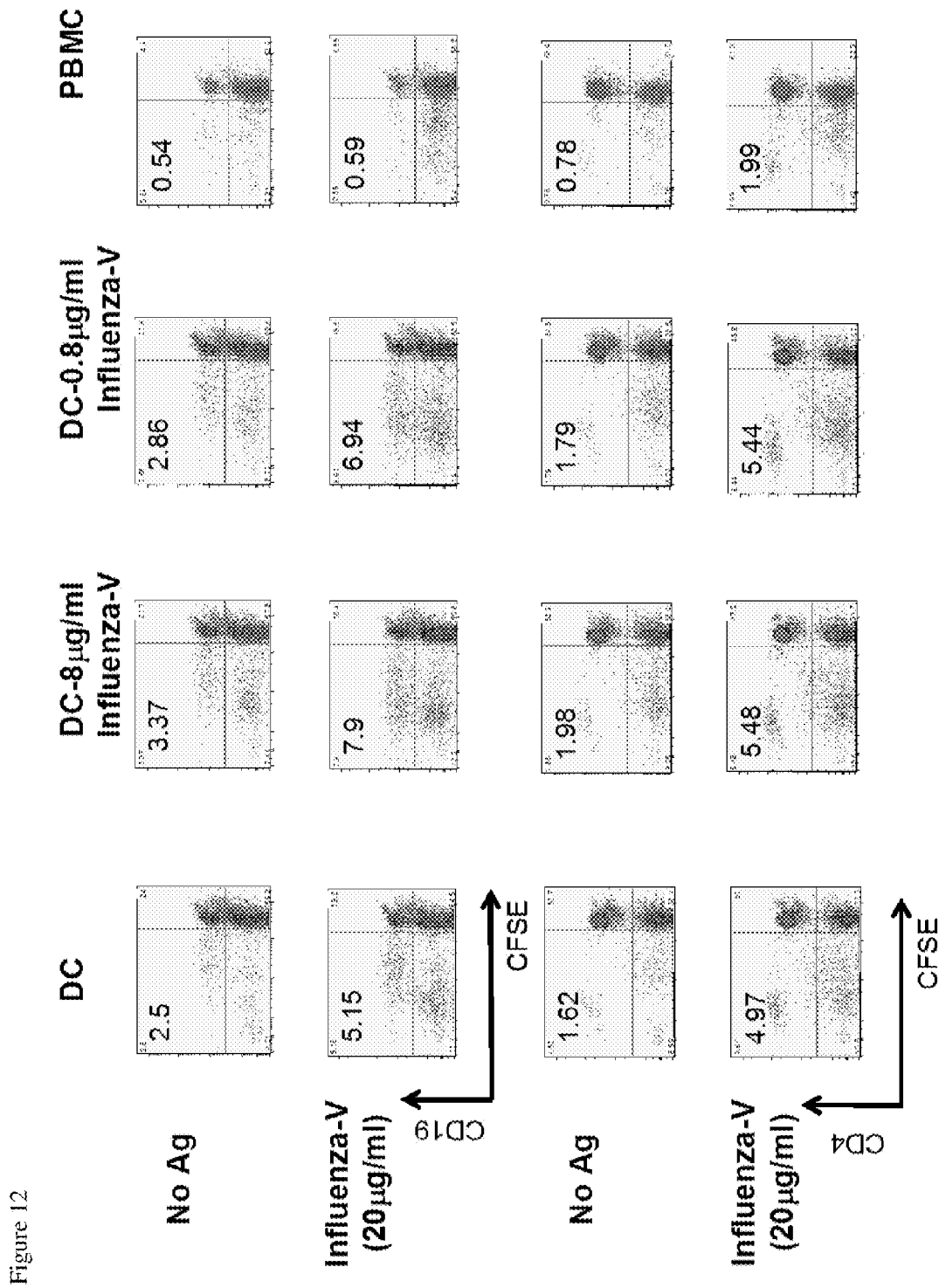
FIG. 12: Shows T and B cell proliferation induced by H1N1 influenza.

In vitro antigen-specific antibody response to influenza (FIG. 11) and T and B cell proliferation induced by H1N1 influenza (FIG. 12). DCs were treated (or not) with H1N1 (New Caledonia) influenza. 2D cultures of DCs and T and B cells were stimulated (or not) with 'soluble' H1N1 influenza. As can be seen, there was antigen-specific proliferation of T and B lymphocytes and generation of antigen-specific antibody secreting B lymphocytes (ELISPOT data). Note the largest (apparently synergistic) response was observed when we pulsed the DCs with antigen and then added soluble antigen to the DC/T and B cell cultures, to activate the B cells, which are antigen-presenting cells (APCs). Again, the T and B cell co-culture is superior to PBMC cultures.

Example 9

In this example, the antigens examined were tetanus toxoid (TT) and a whole protein extract of Candida albicans.

CD4+ T cells, purified by negative magnetic bead selection, were cultured with antigen-pulsed DCs at ~1:60 ratio.

In the first experiment, B cells were added at the same time (day 0) in equal numbers to the T cells, DCs and antigen.

In the second experiment, antigen-primed B cells were added to the T/DC cultures 3 days after the T/DC cultures were established.

As a control, cultures were also established in the absence of any antigen.

Seven days following the addition of the antigen-primed B cells to the T/DC cultures, the cells were harvested and analyzed for antigen-specific B cells by ELISPOT assay.

Figure 13:
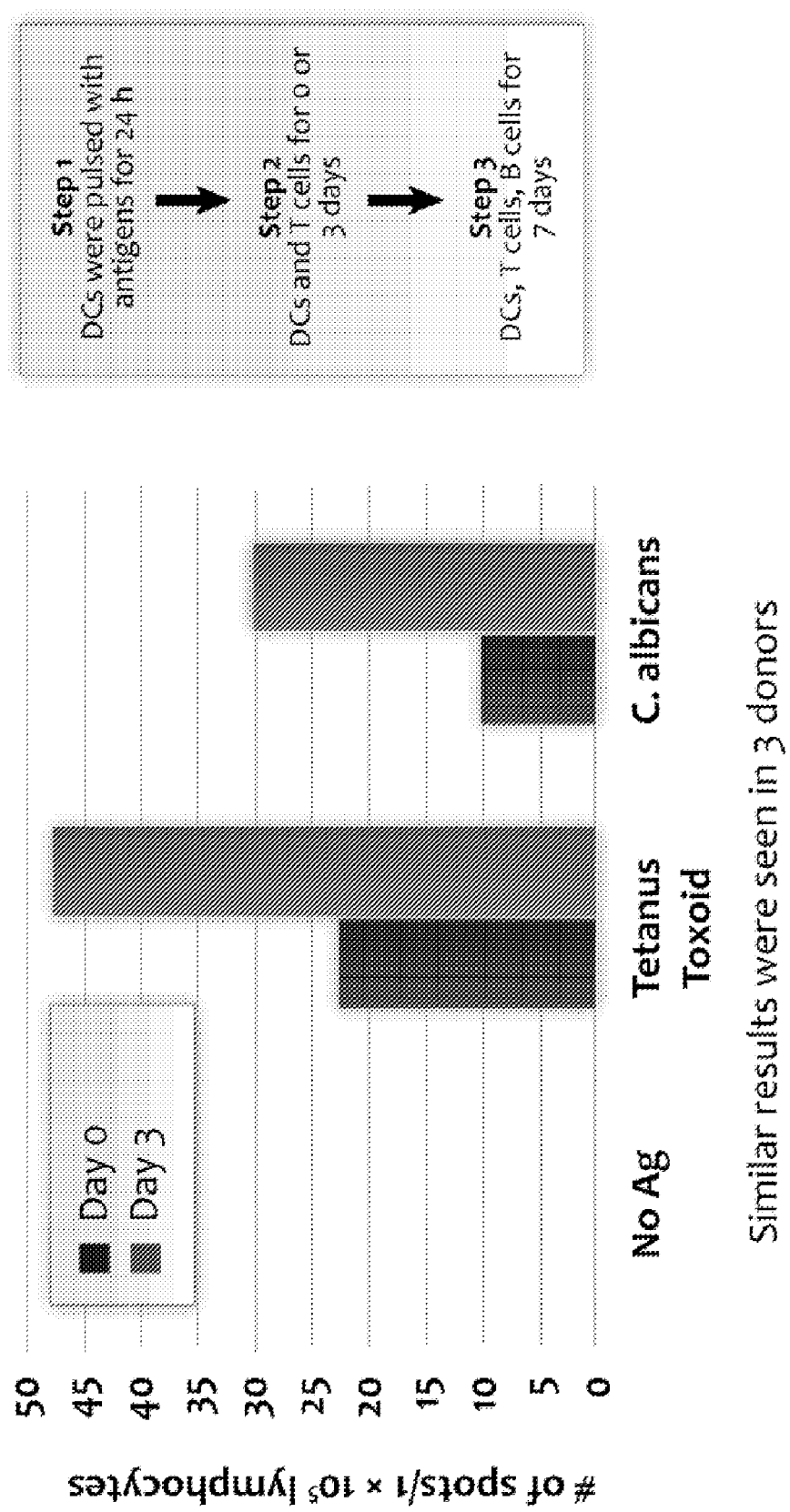
FIG. 13: Shows in vitro the importance of the temporal sequence of immunological events.

As FIG. 13 illustrates, the immune (antibody) response was much stronger in the case where the antigen-primed B cells were added to the T/DC culture after 3 days. Similar results were obtained using cells obtained form three independent blood donors.

Example 10

Figure 14:
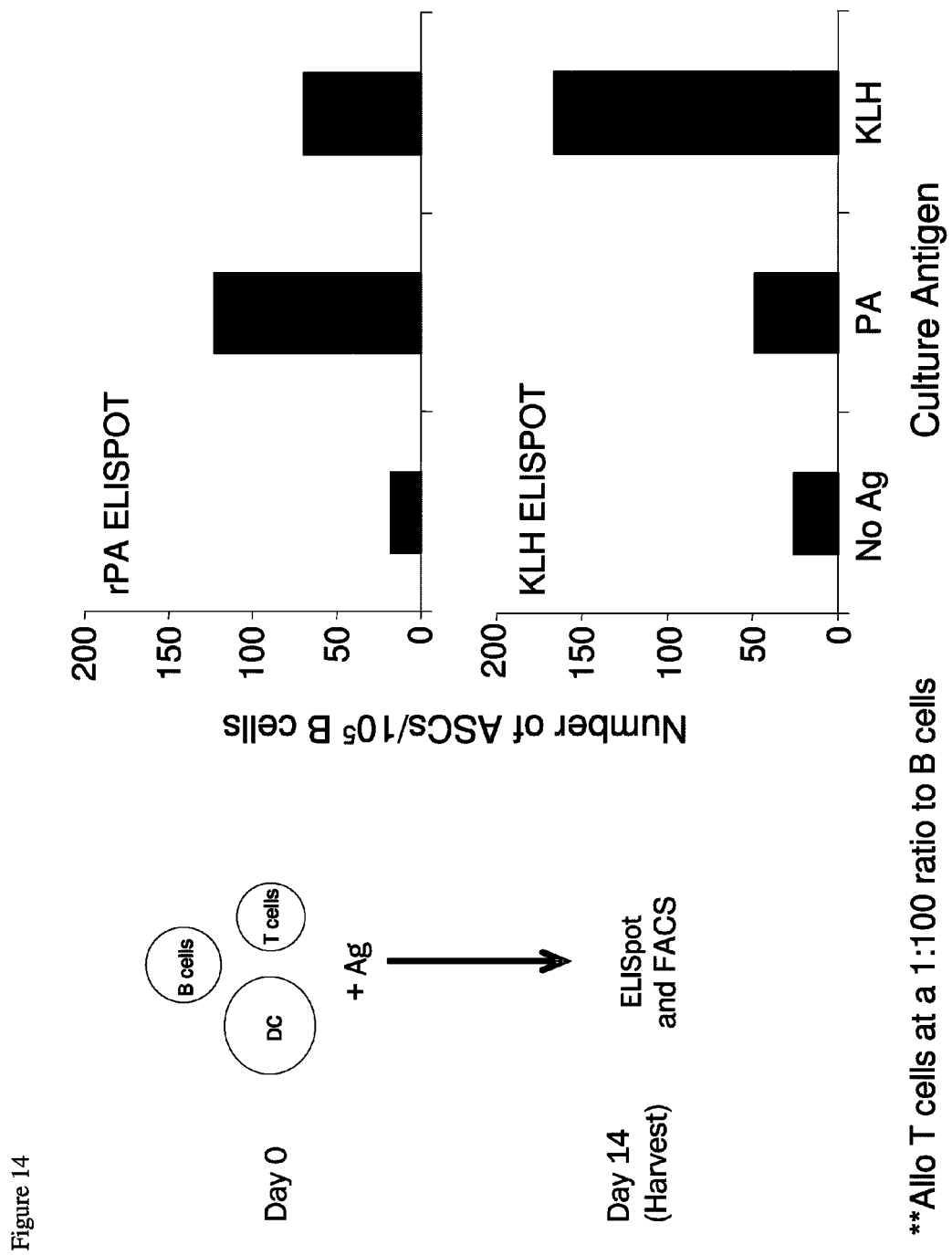
FIG. 14: Shows a rapid assay system for the development of primary B cell responses.

A rapid assay system for the development of primary B cell responses. Antigen-primed dendritic cells (DCs) were cultured with syngeneic B cells (~2 to ~2.5×10$^6$) in 24-well plates and allogeneic CD4+ T cells at a 1:100 ratio (i.e., ~2 to ~2.5×10$^4$ allogeneic T cells). Additional antigen was added (the antigens used were keyhole limpet hemocyanin (KLH) and the anthrax recombinant protective antigen (rPa)). Fourteen days later, the primary B cell response was assessed by ELISPOT and FACS. As FIG. 14 illustrates, the ELISPOT results show that, despite some background, enhanced primary B cell responses (IgM) were observed to the antigens.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A method for immortalizing B cells monoclonal for an antigen, comprising:
   (a) priming a population of dendritic cells with an antigen;
   (b) adding the antigen-primed dendritic cells of (a) to a cell culture comprising T cells and serum-free culture media;
   (c) priming a population of B cells with the antigen;
   (d) adding the antigen-primed B cells of (c) to the cell culture comprising T cells and antigen-primed dendritic cells of (b);
   (e) culturing the cell culture of (d) under conditions promoting production of antibodies by the antigen-primed B cells;
   (f) identifying B cells in the culture of (e) that are monoclonal for the antigen; and
   (g) isolating and immortalizing B cells identified in (f) that are monoclonal for the antigen.

2. The method of claim 1, wherein the serum-free cell culture media is X-VIVO 15.

3. The method of claim 1, further comprising adding the antigen to the cell culture (e).

4. A method for producing antibodies having binding specificity for an antigen, comprising:
   (a) priming a population of dendritic cells with an antigen;
   (b) adding the antigen-primed dendritic cells of (a) to a cell culture comprising T cells and serum-free culture media;
   (c) priming a population of B cells with the antigen;
   (d) adding the antigen-primed B cells of (c) to the cell culture comprising T cells and antigen-primed dendritic cells of (b); and
   (e) culturing the cell culture of (d) under conditions promoting production of antibodies by the antigen-primed B cells.

5. The method of claim 4, further comprising isolating antibodies specific for the antigen from the culture of (e).

6. The method of claim 4, wherein the serum-free cell culture media is X-VIVO 15.

7. The method of claim 4, further comprising adding the antigen to the cell culture (e).

8. A method for immortalizing B cells producing antibodies having binding specificity for an antigen, comprising:
   (a) priming a population of dendritic cells with an antigen;
   (b) adding the antigen-primed dendritic cells of (a) to a cell culture comprising T cells and serum-free cell culture media;
   (c) priming a population of B cells with the antigen;
   (d) adding the antigen-primed B cells of (c) to the cell culture comprising T cells and antigen-primed dendritic cells of (b);
   (e) culturing the cell culture of (d) under conditions promoting production of antibodies by the antigen-primed B cells;
   (f) identifying B cells producing antibodies having binding specificity for the antigen in the culture of (e); and
   (g) isolating and immortalizing B cells identified in (f) producing antibodies having binding specificity for the antigen.

9. The method of claim 8, wherein the serum-free cell culture media is X-VIVO 15.

10. The method of claim 8, further comprising adding the antigen to the cell culture of (e).

11. A method for producing a therapeutic composition comprising monoclonal antibodies having binding specificity for an antigen, the method comprising:
   (a) priming a population of dendritic cells with an antigen;
   (b) adding the antigen-primed dendritic cells of (a) to a cell culture comprising T cells and serum-free cell culture media;
   (c) priming a population of B cells with the antigen;
   (d) adding the antigen-primed B cells of (c) to the cell culture comprising T cells and antigen-primed dendritic cells of (b);
   (e) culturing the cell culture of (d) under conditions promoting production of antibodies by the antigen-primed B cells;
   (f) identifying B cells in the culture of (e) that are monoclonal for the antigen;
   (g) isolating and immortalizing B cells identified in (f) that are monoclonal for the antigen; and
   (h) preparing a therapeutic composition comprising monoclonal antibodies produced by the immortalized B cells of (g) and a pharmaceutically acceptable carrier.

12. A method for producing a therapeutic composition comprising a monoclonal antibody having binding specificity for an antigen, the method comprising:
   (a) priming a population of dendritic cells with an antigen;
   (b) adding the antigen-primed dendritic cells of (a) to a cell culture comprising T cells and serum-free cell culture media;
   (c) priming a population of B cells with the antigen;
   (d) adding the antigen-primed B cells of (c) to the cell culture comprising T cells and antigen-primed dendritic cells of (b);

(e) culturing the cell culture of (d) under conditions promoting production of antibodies by the antigen-primed B cells;
(f) identifying B cells in the culture of (e) that are monoclonal for the antigen;
(g) isolating and immortalizing B cells identified in (f) that are monoclonal for the antigen; and
(h) preparing a therapeutic composition comprising monoclonal antibodies produced by one of the immortalized B cells of (g) and a pharmaceutically acceptable carrier.

13. A method for producing a therapeutic composition comprising antibodies having binding specificity for an antigen, the method comprising:
(a) priming a population of dendritic cells with an antigen;
(b) adding the antigen-primed dendritic cells of (a) to a cell culture comprising T cells and serum-free cell culture media;
(c) priming a population of B cells with the antigen;
(d) adding the antigen-primed B cells of (c) to the cell culture comprising T cells and antigen-primed dendritic cells of (b);
(e) culturing the cell culture of (d) under conditions promoting production of antibodies by the antigen-primed B cells;
(f) identifying B cells in the culture of (e) producing antibodies having binding specificity for the antigen;
(g) isolating and immortalizing B cells identified in (f) having binding specificity for the antigen; and
(h) preparing a therapeutic composition comprising antibodies having binding specificity for the antigen produced by the immortalized B cells of (g) and a pharmaceutically acceptable carrier.

14. A method for preparing a therapeutic composition comprising antibodies having binding specificity for an antigen, the method comprising:
(a) priming a population of dendritic cells with an antigen;
(b) adding the antigen-primed dendritic cells of (a) to a cell culture comprising T cells and serum-free cell culture media;
(c) priming a population of B cells with the antigen;
(d) adding the antigen-primed B cells of (c) to the cell culture comprising T cells and antigen-primed dendritic cells of (b);
(e) culturing the cell culture of (d) under conditions promoting production of antibodies by the antigen-primed B cells;
(f) isolating antibodies specific for the antigen from the culture of (e); and
(g) preparing a therapeutic composition comprising the isolated antibodies of (f) and a pharmaceutically acceptable carrier.

* * * * *